(12) United States Patent
Molt et al.

(10) Patent No.: US 8,383,828 B2
(45) Date of Patent: Feb. 26, 2013

(54) TRANSITION METAL COMPLEXES COMPRISING ONE NONCARBENE LIGAND AND ONE OR TWO CARBENE LIGANDS AND THEIR USE IN OLEDS

(75) Inventors: Oliver Molt, Hirschberg (DE); Evelyn Fuchs, Mannheim (DE); Christian Lennartz, Schifferstadt (DE); Klaus Kahle, Ludwigshafen (DE); Nicolle Moonen, Mannheim (DE); Christian Schildknecht, Dannstadt-Schauernheim (DE); Jens Rudolph, Worms (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 572 days.

(21) Appl. No.: 12/295,999

(22) PCT Filed: Apr. 3, 2007

(86) PCT No.: PCT/EP2007/053262
§ 371 (c)(1),
(2), (4) Date: Oct. 3, 2008

(87) PCT Pub. No.: WO2007/115981
PCT Pub. Date: Oct. 18, 2007

(65) Prior Publication Data
US 2009/0054657 A1 Feb. 26, 2009

(30) Foreign Application Priority Data
Apr. 4, 2006 (EP) .................................... 06112198

(51) Int. Cl.
*C07F 15/00* (2006.01)
(52) U.S. Cl. ...................................................... 548/103
(58) Field of Classification Search .................. 548/103
See application file for complete search history.

(56) References Cited

U.S. PATENT DOCUMENTS

| | | | | |
|---|---|---|---|---|
| 7,902,374 | B2 * | 3/2011 | Lin et al. | 548/103 |
| 2006/0251923 | A1 * | 11/2006 | Lin et al. | 428/690 |
| 2006/0258043 | A1 | 11/2006 | Bold et al. | |
| 2007/0088167 | A1 * | 4/2007 | Lin et al. | 548/103 |
| 2007/0282076 | A1 | 12/2007 | Bold et al. | |
| 2010/0213834 | A1 | 8/2010 | Molt et al. | |
| 2011/0114922 | A1 * | 5/2011 | Pretot et al. | 257/40 |

FOREIGN PATENT DOCUMENTS

| | | |
|---|---|---|
| WO | 2005 019373 | 3/2005 |
| WO | 2005 113704 | 12/2005 |
| WO | 2006 018292 | 2/2006 |
| WO | WO 2006/067074 A2 * | 6/2006 |
| WO | WO 2006/106842 A1 * | 10/2006 |

OTHER PUBLICATIONS

U.S. Appl. No. 12/597,651, filed Oct. 26, 2009, Moonen, et al.
U.S. Appl. No. 12/667,765, filed Jan. 5, 2010, Langer, et al.
U.S. Appl. No. 12/667,619, filed Jan. 4, 2010, Langer, et al.

* cited by examiner

*Primary Examiner* — Joseph Kosack
(74) *Attorney, Agent, or Firm* — Oblon, Spivak, McClelland, Maier & Neustadt, L.L.P.

(57) ABSTRACT

The present invention relates to heteroleptic carbene complexes comprising both carbene ligands and heterocyclic noncarbene ligands, to a process for preparing the heteroleptic carbene complexes, to the use of the heteroleptic carbene complexes in organic light-emitting diodes, to organic light-emitting diodes comprising at least one inventive heteroleptic carbene complex, to a light-emitting layer comprising at least one inventive heteroleptic carbene complex, to organic light-emitting diodes comprising at least one inventive light-emitting layer, and to devices which comprise at least one inventive organic light-emitting diode.

14 Claims, No Drawings

TRANSITION METAL COMPLEXES COMPRISING ONE NONCARBENE LIGAND AND ONE OR TWO CARBENE LIGANDS AND THEIR USE IN OLEDS

The present invention relates to heteroleptic carbene complexes comprising both carbene ligands and heterocyclic noncarbene ligands, to a process for preparing the heteroleptic carbene complexes, to the use of the heteroleptic carbene complexes in organic light-emitting diodes, to organic light-emitting diodes comprising at least one inventive heteroleptic carbene complex, to a light-emitting layer comprising at least one inventive heteroleptic carbene complex, to organic light-emitting diodes comprising at least one inventive light-emitting layer, and to devices which comprise at least one inventive organic light-emitting diode.

In organic light-emitting diodes (OLEDs), the property of materials to emit light when they are excited by electrical current is exploited. OLEDs are of interest especially as an alternative to cathode ray tubes and liquid-crystal displays for the production of flat visual display units. Owing to the very compact design and the intrinsically low electricity consumption, the devices comprising OLEDs are especially suitable for mobile applications, for example for uses in cell phones, laptops, etc.

The basic principles of the functioning of OLEDs and suitable assemblies (layers) of OLEDs are specified, for example, in WO 2005/113704 and the literature cited therein.

The prior art has already proposed numerous materials which emit light on excitation by electrical current.

WO 2005/019373 for the first time discloses the use of uncharged transition metal complexes which comprise at least one carbene ligand in OLEDs. According to WO 2005/019373, these transition metal complexes can be used in any layer of an OLED, the ligand structure or central metal being variable for adjustment to the desired properties of the transition metal complexes. For example, the use of the transition metal complexes in a blocking layer for electrons, a blocking layer for excitons, a blocking layer for holes, or the light-emitting layer of the OLED is possible, preference being given to using the transition metal complexes as emitter molecules in OLEDs.

WO 2005/113704 relates to luminescent compounds which bear carbene ligands. WO 2005/113704 specifies numerous transition metal complexes with different carbene ligands, preference being given to using the transition metal complexes as phosphorescent light-emitting material, more preferably as a doping substance.

Even though compounds suitable for use in OLEDs, especially as light-emitting substances, are already known, the provision of more efficient compounds which are useable industrially is desirable. In the context of the present application, the electro-luminescence refers both to electrofluorescence and to electrophosphorescence.

It is therefore an object of the present application to provide novel carbene complexes which are suitable for use in OLEDs. In particular, the provision of transition metal complexes which exhibit an improved property spectrum compared to known transition metal complexes, for example improved efficiencies and/or an improved lifetime is desirable.

This object is achieved by the provision of heteroleptic carbene complexes of the general formula (I)

$$M^1[\text{carbene}]_n[\text{het}]_m \qquad (I)$$

comprising both carbene ligands and heterocyclic noncarbene ligands, in which the symbols are each defined as follows:

$M^1$ is a metal atom selected from the group consisting of Ir, Co, Rh, Ni, Pd, Pt, Fe, Ru, Os, Cr, Mo, W, Mn, Tc, Re, Cu and Au, preferably Ir, Os, Ru, Rh, Pd, Co and Pt, more preferably Ir, Pt, Rh and Os, most preferably Ir, in any oxidation state possible for the corresponding metal atom;

n is the number of carbene ligands, where n, in the case that the sum of (n+m)=2, is 1 and, in the case that the sum of (n+m)≧3, is at least 2, where the carbene ligands in the case where n is at least 2 may be the same or different;

m is the number of heterocyclic noncarbene ligands, where m≧1, where the heterocyclic noncarbene ligands may be the same or different in the case when m>1;

where n and m are dependent on the oxidation state and coordination number of the metal atom used and on the charge of the carbene and het ligands; carbene is a carbene ligand of the general formula (II)

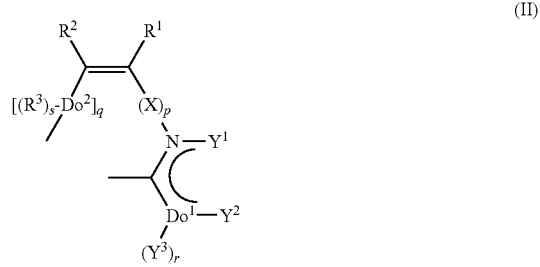

where the symbols in the carbene ligand of the general formula II are each defined as follows:

$Do^1$ is a donor atom selected from the group consisting of C, P, N, O, S and Si, preferably P, N, O and S;

$Do^2$ is a donor atom selected from the group consisting of C, N, P, O and S;

r is 2 when $Do^1$ is C or Si, is 1 when $Do^1$ is N or P, and is 0 when $Do^1$ is O or S;

s is 2 when $Do^2$ is C, is 1 when $Do^2$ is N or P, and is 0 when $Do^2$ is O or S;

X is a spacer selected from the group consisting of silylene, alkylene, arylene, heteroarylene, alkynylene, alkenylene, $NR^{13}$, $PR^{14}$, $BR^{15}$, O, S, SO, $SO_2$, CO, CO—O, O—CO and $(CR^{16}R^{17})_w$, where one or more nonadjacent $(CR^{16}R^{17})$ groups may be replaced by $NR^{13}$, $PR^{14}$, $BR^{15}$, O, S, SO, $SO_2$, CO, CO—O, O—CO;

w is from 2 to 10;

$R^{13}$, $R^{14}$, $R^{15}$, $R^{16}$, $R^{17}$ are each
H, alkyl, aryl, heteroaryl, alkenyl, alkynyl;

p is 0 or 1;

q is 0 or 1;

$Y^1$, $Y^2$ are each independently hydrogen or a carbon group selected from the group consisting of alkyl, aryl, heteroaryl, alkynyl and alkenyl groups;

or $Y^1$ and $Y^2$ together form a bridge between the donor atom $Do^1$ and the nitrogen atom N, said bridge having at least two atoms of which at least one is a carbon atom, $R^1$, $R^2$ are each independently hydrogen, alkyl, aryl, heteroaryl, alkynyl or alkenyl radicals, or $R^1$ and $R^2$ together form a bridge having a total of from three to five atoms, of which from 1 to 5 atoms may be heteroatoms and the remaining atoms are carbon atoms, so that the group

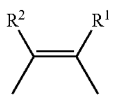

forms a five- to seven-membered ring which, if appropriate—in addition to the double bond already present—may have one further double bond or—in the case of a six- or seven-membered ring—two further double bonds, and may optionally be substituted by alkyl or aryl groups and/or groups with donor or acceptor action, and may optionally comprise at least one heteroatom, and the five- to seven-membered ring may optionally be fused to one or more further rings;

in addition, $Y^1$ and $R^1$ may be bonded to one another via a bridge, where the bridge may be defined as follows:

alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;

and $R^{18}$, $R^{19}$, $R^{20}$, $R^{21}$, $R^{22}$, $R^{30}$, $R^{31}$ are each H, alkyl, aryl, heteroaryl, alkenyl, alkynyl;

$R^3$ is hydrogen, an alkyl, aryl, heteroaryl, alkynyl or alkenyl radical;

$Y^3$ is hydrogen, an alkyl, alkynyl or alkenyl radical, or

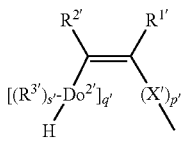

where $Do^{2'}$, q', s', $R^{3'}$, $R^{1'}$, $R^{2'}$, X' and p' are each independently as defined for $Do^2$, q, s, $R^3$, $R^1$, $R^2$, X and p;

in addition, $Y^3$ and $Y^2$ in each of the n carbene ligands may be bonded to one another via a bridge, where the bridge may be defined as follows:

alkylene, arylene, heteroarylene, alkynylene, alkenylene, $NR^{25}$, $PR^{26}$, $BR^{27}$, O, S, SO, $SO_2$, $SiR^{32}R^{33}$, CO, CO—O, O—CO and $(CR^{28}R^{29})_y$, where one or more nonadjacent $(CR^{28}R^{29})$ groups may be replaced by $NR^{25}$, $PR^{26}$, $BR^{27}$, O, S, SO, $SO_2$, $SiR^{32}R^{33}$, CO, CO—O, O—CO, where y is from 2 to 10;

and $R^{25}$, $R^{26}$, $R^{27}$, $R^{28}$, $R^{29}$, $R^{32}$, $R^{33}$ are each H, alkyl, aryl, heteroaryl, alkenyl, alkynyl;

and het is a heterocyclic noncarbene ligand of the general formula (III)

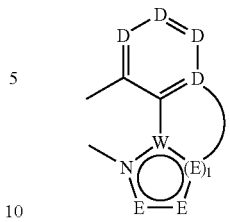

(III)

in which the symbols in the ligand het of the general formula III are each defined as follows:

D are each independently $CR^{34}$ or N;

W is C, N, P;

E are each independently $CR^{35}$, N, $NR^{36}$, S, O, P or $PR^{37}$;

l is 1 or 2;

$R^{34}$, $R^{35}$, $R^{36}$, $R^{37}$ are each independently H, an alkyl, aryl, heteroaryl, alkynyl or alkenyl radical, or in each case 2 $R^{34}$, $R^{35}$, $R^{36}$ or $R^{37}$ radicals together form a fused ring which may optionally comprise at least one heteroatom, or $R^{34}$, $R^{35}$, $R^{36}$ or $R^{37}$ is a radical having donor or acceptor action;

where the dotted line means an optional bridge between one of the D groups and one of the E groups; where the bridge may be defined as follows:

alkylene, arylene, heteroarylene, alkynylene, alkenylene, $NR^{38}$, $PR^{39}$, $BR^{40}$, O, S, SO, $SO_2$, $SiR^{41}R^{42}$, CO, CO—O, O—CO and $(CR^{43}R^{44})_v$, where one or more nonadjacent $(CR^{43}R^{44})$ groups may be replaced by $NR^{38}$, $PR^{39}$, $BR^{40}$, O, S, SO, $SO_2$, $SiR^{41}R^{42}$, CO, CO—O, O—CO, where v is from 2 to 10;

and $R^{38}$, $R^{39}$, $R^{40}$, $R^{41}$, $R^{42}$, $R^{43}$, $R^{44}$ are each H, alkyl, aryl, heteroaryl, alkenyl, alkynyl.

The inventive heteroleptic carbene complexes of the formula I are thus notable in that they have at least one carbene ligand of the general formula II and at least one heterocyclic noncarbene ligand of the general formula III. Depending on the oxidation state and coordination number of the metal atom $M^1$ used and on the charge of the ligands, further carbene ligands of the general formula II may be present in the inventive heteroleptic carbene complex as well as the at least one carbene ligand of the general formula II and the at least one heterocyclic noncarbene ligand of the general formula III, where the substitution patterns of the individual carbene ligands of the general formula II may be the same or different. In the case when $M^1$ is a metal with a coordination number of 4 (e.g. Pt(II) or Pd(II), Ir(I), Rh(I)), the inventive heteroleptic carbene complexes have one carbene ligand of the general formula II and one heterocyclic noncarbene ligand of the general formula III. In the case when $M^1$ is a metal with a coordination number of 6 (e.g. Ir(III), Co(II), Co(III), Rh(III), Os(II), Pt(IV)), the inventive heteroleptic carbene complexes have two carbene ligands of the general formula II, which may be the same or different, and one heterocyclic noncarbene ligand of the general formula III. When the metal atom $M^1$ has a coordination number of 8 or more, the heteroleptic carbene complexes of the general formula I, in addition to two carbene ligands of the general formula II and one heterocyclic noncarbene ligand of the general formula III, may have either one or more further carbene ligands of the general formula II and/or one or more heterocyclic noncarbene ligands of the general formula III. In a preferred embodiment, the present invention relates to heteroleptic carbene complexes of the general formula I which have a metal $M^1$ with a coordination number of 6, two carbene ligands of the general formula II and a heterocyclic noncarbene ligand of the general formula III.

It has been found that the inventive heteroleptic carbene complexes which comprise at least one carbene ligand of the general formula II and at least one heterocyclic noncarbene ligand, in particular the inventive heteroleptic carbon complexes which have a plurality of carbene ligands of the general formula II, when they are used in organic light-emitting diodes (OLEDs), are notable in that they exhibit surprisingly high quantum yields. With the aid of the specific ligand combination of the inventive heteroleptic carbene complexes, it is additionally possible to achieve a red shift in the emission compared to pure carbene complexes. The inventive heteroleptic carbene complexes can thus be used in OLEDs for a controlled color adjustment with high quantum yield.

Depending on the coordination number of the metal $M^1$ used and the number of carbene ligands and non-carbene ligands used, different isomers of the corresponding metal complexes may be present for the same metal $M^1$ and the same nature of the carbene ligands and non-carbene ligands used. For example, in the case of complexes with a metal $M^1$ of coordination number 6 (i.e. octahedral complexes), for example Ir(III) complexes, "fac-mer isomers" (facial/meridional isomers) are possible when the complexes are of the general composition $M(AB)_2(CD)$ where AB and CD are bidentate ligands. In the context of the present application, "fac-mer isomers" refer to the isomers shown below:

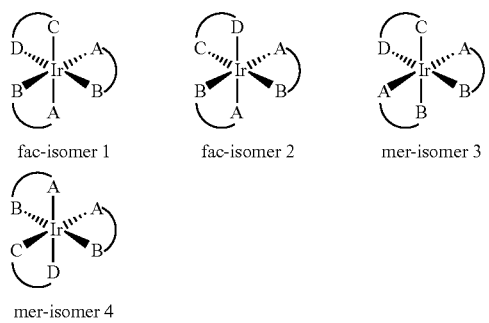

fac-isomer 1    fac-isomer 2    mer-isomer 3 mer-isomer 4

In square-planar complexes with a metal $M^1$ of coordination number 4, for example Pt(II) complexes, "isomers" are possible when the complexes are of the general composition M(AB)(CD) where AB and CD are bidentate ligands. In the context of the present application, "isomers" are understood to mean the isomers shown below:

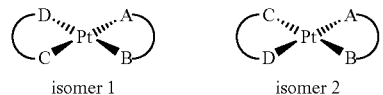

isomer 1    isomer 2

The symbols A and B, and C and D, are each one binding site of a ligand, only bidentate ligands being present. According to the aforementioned general composition, a bidentate ligand has an A group and a B group, or a C group and a D group.

It is known in principle to those skilled in the art what is meant by cis/trans and fac-mer isomers. In complexes of the composition $MA_3B_3$, three groups of the same type can either occupy the corners of an octahedral face (facial isomer) or a meridian, i.e. two of the three ligand binding sites are trans relative to one another (meridional isomer). With regard to the definition of cis/trans isomers and fac-mer isomers in octahedral metal complexes, see, for example, J. Huheey, E. Keiter, R. Keiter, Anorganische Chemie: Prinzipien von Struktur und Reaktivität [Inorganic chemistry: Principles of Structure and Reactivity], 2nd, newly revised edition, translated into German and expanded by Ralf Steudel, Berlin; New York: de Gruyter, 1995, pages 575, 576.

In square-planar complexes, cis isomerism means that, in complexes of the composition $MA_2B_2$, both the two A groups and the two B groups occupy adjacent corners of a square, while both the two A groups and the two B groups in trans isomerism each occupy the two mutually diagonal corners of a square. With regard to the definition of cis/trans isomers in square-planar metal complexes, see, for example, J. Huheey, E. Keiter, R. Keiter, Anorganische Chemie: Prinzipien von Struktur und Reaktivität, 2nd, newly revised edition, translated into German and expanded by Ralf Steudel, Berlin; New York: de Gruyter, 1995, pages 557 to 559.

In general, the different isomers of the metal complexes of the formula I can be separated by processes known to those skilled in the art, for example by chromatography, sublimation or crystallization.

The present invention therefore relates in each case both to the individual isomers of the carbene complexes of the formula I and to mixtures of different isomers in any mixing ratio.

The inventive heteroleptic carbene complexes of the general formula I more preferably have a metal atom $M^1$ selected from the group consisting of Ir, Os, Rh and Pt, very particular preference being given to Os(II), Rh(III), Ir(III) and Pt(II). Ir(III) is very especially preferred.

The number n of carbene ligands of the general formula II in the inventive heteroleptic carbene complexes of the formula I in which the transition metal atom $M^1$ has a coordination number of 6, particular preference being given to Ir(III), is 2 and the number m of the heterocyclic noncarbene ligand of the general formula III in these complexes is 1.

The number n of carbene ligands of the general formula II in transition metal complexes in which the transition metal atom $M^1$ has a coordination number of 4, particular preference being given to Pt(II), is 1 and the number m of the heterocyclic noncarbene ligand of the general formula III in these complexes is likewise 1.

For the $Y^1$ and $Y^2$ groups, in the context of the present application:
the substituents of the $Y^1$ and $Y^2$ groups may together form a bridge having a total of from two to four, preferably from two to three, atoms, of which one or two atoms may be heteroatoms, preferably N, and the remaining atoms are carbon atoms, so that the $NCDo^1$ moiety, together with this bridge, form a five- to seven-membered, preferably five- to six-membered, ring which may optionally have two or—in the case of a six- or seven-membered ring—three double bonds and may optionally be substituted by alkyl or aryl groups and/or groups with donor or acceptor action, and may optionally comprise heteroatoms, preferably N, preference being given to a five-membered or six-membered aromatic ring which is substituted by alkyl or aryl groups and/or groups with donor or acceptor action or is unsubstituted, or the preferred five-membered or six-membered aromatic ring is fused to further rings which may optionally comprise at least one heteroatom, preferably N, preferably six-membered aromatic rings.

The $Y^1$ group may be bonded to the $R^1$ radical via a bridge, where the bridge may be defined as follows:

Alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$ where one or more nonadjacent CO—O, O—CO, where x is from 2 to 10;

and $R^{18}$, $R^{19}$, $R^{20}$, $R^{21}$, $R^{22}$, $R^{30}$, $R^{31}$ are each H, alkyl, aryl, heteroaryl, alkenyl, alkynyl.

In the case that $Y^1$ and $Y^2$ together form a bridge to form a five- to seven-membered ring, the bridge which bonds it to the $R^1$ radical may be bonded directly to the five- to seven-membered ring or be bonded to a substituent of this ring, preference being given to a direct bond to the five- to seven-membered ring. The atom directly adjacent to the nitrogen atom (in the general formula II) of the five- to seven-membered ring is more preferably bonded to $R^1$ via a bridge when such a bond is present (see, for example, the bridged structures hereinafter). In the case that the five- to seven-membered ring formed by a common bridge of $Y^1$ and $Y^2$ is fused to a further five- to seven-membered ring, the joining bridge can be bonded to an atom of the fused ring (see, for example, the bridged structures hereinafter).

Preferred bridged structures are specified hereinafter by way of example for the carbene ligands of the general formula II. The groups shown in the ligand systems shown may, for example, bear substituents, or one or more CH groups in the aromatic groups shown may be replaced by heteroatoms. It is likewise possible that the carbene ligands have a plurality of identical or different bridges. The bridges shown may also occur in other ligand systems used in accordance with the invention, for example in the ligand systems of the formulae aa to ae mentioned below.

Examples of carbene ligands with bridged structures:

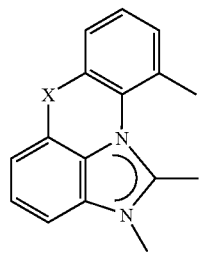
X = O, S, SO, $SO_2$, $CH_2CMe_2$, $SiR^{30}R^{31}$, NMe

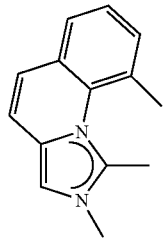

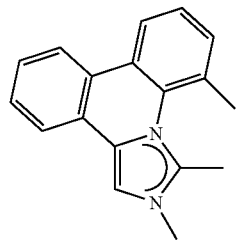
X = O, S, SO, $SO_2$, $CH_2$, $CMe_2$, $SiR^{30}R^{31}$, NMe

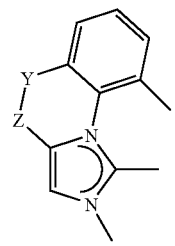
Y-Z = 1x $CR^{21}R^{22}$ and 1x O, S, SO, $SO_2$, $CR^{21}R^{22}$, $SiR^{30}R^{31}$, $NR^{18}$ or Y-Z = CO—O, O—CO

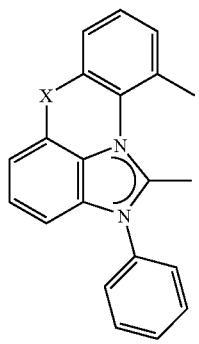
X = O, S, SO, $SO_2$, $CH_2$ $CMe_2$, $SiR^{30}R^{31}$, NMe

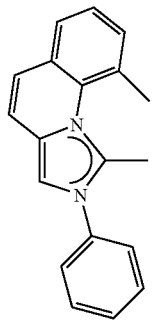

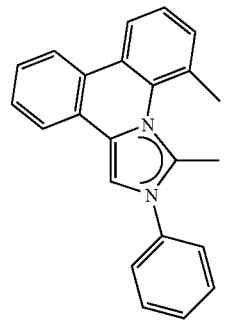

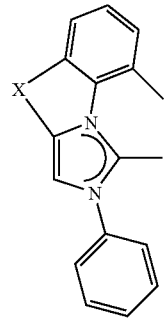
X = O, S, SO, $SO_2$, $CH_2$, $CMe_2$, $SiR^{30}R^{31}$, NMe

Y-Z = 1x $CR^{21}R^{22}$ and 1x O, S, SO, $SO_2$, $CR^{21}R^{22}$, $SiR^{30}R^{31}$, $NR^{18}$ or Y-Z = CO—O, O—CO

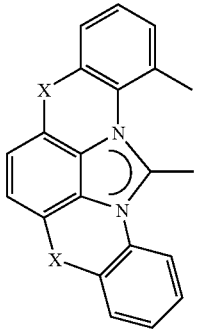
X = O, S, SO, $SO_2$, $CH_2$ $CMe_2$, $SiR^{30}R^{31}$, NMe

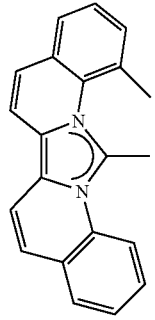

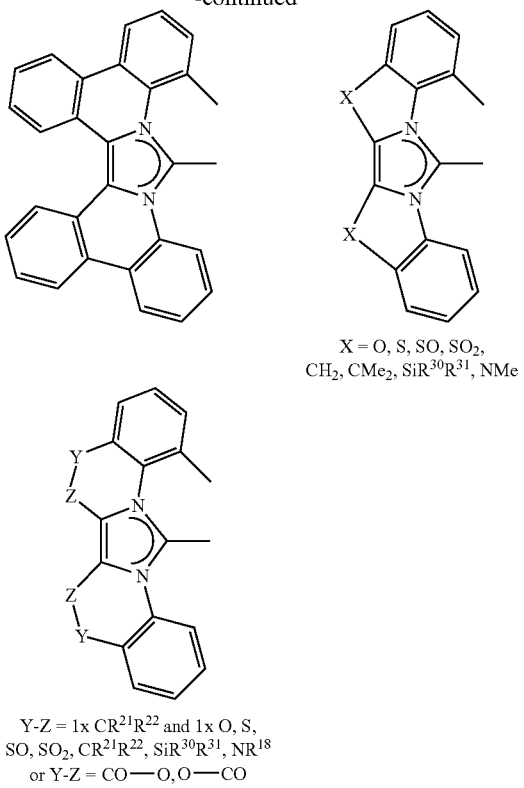

The $R^{18}$, $R^{21}$, $R^{22}$, $R^{30}$ and $R^{31}$ radicals have already been defined above.

In the context of the present application, the terms aryl radical or group, heteroaryl radical or group, alkyl radical or group, and alkenyl radical or group, and alkynyl radical or group are each defined as follows:

An aryl radical (or group) is understood to mean a radical with a base structure of from 6 to 30 carbon atoms, preferably from 6 to 18 carbon atoms, which is formed from an aromatic ring or a plurality of fused aromatic rings. Suitable base structures are, for example, phenyl, naphthyl, anthracenyl or phenanthrenyl. This base structure may be unsubstituted (i.e. all carbon atoms which are substitutable bear hydrogen atoms) or be substituted at one, more than one or all substitutable positions of the base structure. Suitable substituents are, for example, alkyl radicals, preferably alkyl radicals having from 1 to 8 carbon atoms, more preferably methyl, ethyl or i-propyl, aryl radicals, preferably $C_6$-aryl radicals, which may in turn be substituted or unsubstituted, heteroaryl radicals, preferably heteroaryl radicals which comprise at least one nitrogen atom, more preferably pyridyl radicals, alkenyl radicals, preferably alkenyl radicals which bear a double bond, more preferably alkenyl radicals having a double bond and from 1 to 8 carbon atoms, or groups with donor or acceptor action. Suitable groups with donor or acceptor action are specified below. Most preferably, the aryl radicals bear substituents selected from the group consisting of methyl, F, Cl, CN, aryloxy and alkoxy, sulfonyl, heteroaryl. The aryl radical or the aryl group is preferably a $C_6$-$C_{18}$-aryl radical, more preferably a $C_6$-aryl radical, which is optionally substituted by at least one of the aforementioned substituents. The $C_6$-$C_{18}$-aryl radical, preferably $C_6$-aryl radical, more preferably has one or two of the aforementioned substituents, where, in the case of a $C_6$-aryl radical, one substituent may be arranged in the ortho, meta or para position to the further bonding site of the aryl radical, and—in the case of two substituents—they may each be arranged in the meta position or ortho position to the further bonding site of the aryl radical, or one radical is arranged in the ortho position and one radical in the meta position, or one radical is arranged in the ortho or meta position and the further radical is arranged in the para position.

A heteroaryl radical or a heteroaryl group is understood to mean radicals which differ from the aforementioned aryl radicals in that at least one carbon atom in the base structure of the aryl radicals is replaced by a heteroatom. Preferred heteroatoms are N, O and S. Most preferably, one or two carbon atoms of the base structure of the aryl radicals are replaced by heteroatoms. Especially preferably, the base structure is selected from systems such as pyridine and five-membered heteroaromatics such as pyrrole, furan, pyrazole, imidazole, thiophene, oxazole, thiazole. The base structure may be substituted at one, more than one or all substitutable positions of the base structure. Suitable substituents are the same as have already been mentioned for the aryl groups.

An alkyl radical or an alkyl group is understood to mean a radical having from 1 to 20 carbon atoms, preferably from 1 to 10 carbon atoms, more preferably from 1 to 8 carbon atoms. This alkyl radical may be branched or unbranched and optionally be interrupted by one or more heteroatoms, preferably Si, N, O or S, more preferably N, O or S. In addition, this alkyl radical may be substituted by one or more of the substituents mentioned for the aryl groups. It is likewise possible that the alkyl radical bears one or more (hetero)aryl groups. In this context, all of the (hetero)aryl groups listed above are suitable. The alkyl radicals are more preferably selected from the group consisting of methyl, ethyl, isopropyl, n-propyl, n-butyl, isobutyl and tert-butyl; very particular preference is given to methyl and isopropyl.

An alkenyl radical or an alkenyl group is understood to mean a radical which corresponds to the aforementioned alkyl radicals having at least two carbon atoms, with the difference that at least one C—C single bond of the alkyl radical has been replaced by a C—C double bond. The alkenyl radical preferably has one or two double bonds.

An alkynyl radical or an alkynyl group is understood to mean a radical which corresponds to the aforementioned alkyl radicals having at least two carbon atoms, with the difference that at least one C—C single bond of the alkyl radical has been replaced by a C—C triple bond. The alkynyl radical preferably has one or two triple bonds.

In the context of the present application, the terms alkylene, arylene, heteroarylene, alkynylene and alkenylene are each as defined for the alkyl, aryl, heteroaryl, alkynyl and alkenyl radicals, with the difference that the alkylene, arylene, heteroarylene, alkynylene and alkenylene groups each have two binding sites to atoms of the ligand of the formula II.

A bridge which is formed from $Y^1$ and $Y^2$ and has at least two atoms, of which at least one is a carbon atom, and the further atoms are preferably nitrogen or carbon atoms, where the bridge may be saturated or preferably unsaturated and the at least two atoms of the bridge may be substituted or unsubstituted, is preferably understood to mean the following groups:

A bridge which has two carbon atoms or one carbon atom and one nitrogen atom, where the carbon atoms or one carbon atom and one nitrogen atom are bonded to one another by a double bond, so that the bridge has one of the following formulae, where the bridge preferably has two carbon atoms:

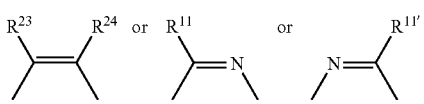

R²³, R²⁴, R¹¹ and R¹¹' are each independently hydrogen, alkyl, heteroaryl, alkenyl, alkynyl, aryl or a substituent with donor or acceptor action, or R²³ and R²⁴ together form a bridge having a total of from 3 to 5, preferably 4, atoms, of which from 1 to 5 atoms may optionally be heteroatoms, preferably N, and the remaining atoms are carbon atoms, so that this group forms a 5- to 7-membered, preferably six-membered, ring which optionally—in addition to the double bond already present—may have one further double bond or—in the case of a six- or seven-membered ring—may have two further double bonds, and may optionally be substituted by alkyl or aryl groups and/or groups with donor or acceptor action. Preference is given to a six-membered aromatic ring. This may be substituted by alkyl or aryl groups and/or groups with donor or acceptor action, or be unsubstituted. In addition, it is possible that one or more further aromatic rings are fused to this preferably six-membered aromatic ring. In this context, any conceivable fusion is possible. These fused radicals may in turn be substituted, preferably by the radicals specified in the general definition of the aryl radicals.

A bridge which has two carbon atoms, where the carbon atoms are bonded to one another by a single bond, so that the bridge has the following formula:

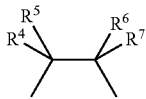

in which R⁴, R⁵, R⁶ and R⁷ are each independently hydrogen, alkyl, heteroaryl, alkenyl, alkynyl, aryl or a substituent with donor or acceptor action, preferably hydrogen, alkyl or aryl.

In the context of the present application, a group or a substituent having donor or acceptor action is understood to mean the following groups:

Groups with donor action are understood to mean groups which have a +I and/or +M effect, and groups with acceptor action are understood to mean groups which have a −I and/or −M effect. Suitable groups with donor or acceptor action are halogen radicals, preferably F, Cl, Br, more preferably F, alkoxy radicals, aryloxy radicals, carbonyl radicals, ester radicals, both oxycarbonyl and carbonyloxy, amine radicals, amide radicals, CH₂F groups, CHF₂ groups, CF₃ groups, CN groups, thio groups, sulfonic acid groups, sulfonic ester groups, boronic acid groups, boronic ester groups, phosphonic acid groups, phosphonic ester groups, phosphine radicals, sulfoxide radicals, sulfonyl radicals, sulfide radicals, heteroaryl radicals, nitro groups, OCN, borane radicals, silyl groups, stannate radicals, imino groups, hydrazine radicals, hydrazone radicals, oxime radicals, nitroso groups, diazo groups, phosphine oxide groups, hydroxyl groups or SCN groups. Very particular preference is given to F, Cl, CN, aryloxy, alkoxy, sulfonyl and heteroaryl.

In the carbene ligands of the general formula II, the moiety

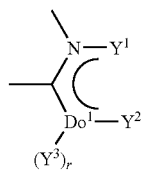

is preferably selected from the group consisting of

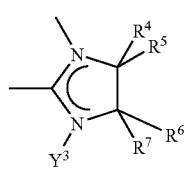

a

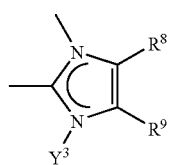

b

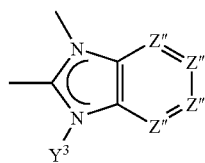

c

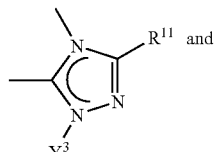

d and

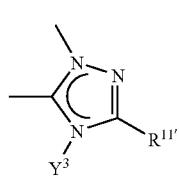

e in which the symbols are each defined as follows:
Z" are each independently CR¹⁰ or N; preferably, from 0 to 3 of the Z" groups are N, more preferably from 0 to 2, most preferably 0 or 1, where the remaining Z" groups are CR¹⁰;
R⁴, R⁵, R⁶, R⁷, R⁸, R⁹, R¹¹ and R¹¹' are each hydrogen, alkyl, aryl, heteroaryl, alkynyl or alkenyl or a substituent with donor or acceptor action, preferably hydrogen, alkyl, heteroaryl or aryl;
R¹⁰ is hydrogen, alkyl, aryl, heteroaryl, alkynyl or alkenyl, or in each case 2 R¹⁰ radicals together form a fused ring which may optionally comprise at least one heteroatom, preferably N, or R¹⁰ is a radical with donor or acceptor action;
in addition, R⁴ or R⁵ in the moiety a, R⁸ in the moiety b, one of the R¹⁰ radicals in the moiety c and R¹¹ in the moiety d may be bonded to R¹ via a bridge, where the bridge may be defined as follows:
alkylene, arylene, heteroarylene, alkynylene, alkenylene, NR¹⁸, PR¹⁹, BR²⁰, O, S, SO, SO₂, SiR³⁰R³¹, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;

and $R^{18}$, $R^{19}$, $R^{20}$, $R^{21}$, $R^{22}$, $R^{30}$, $R^{31}$ are each H, alkyl, aryl, heteroaryl, alkenyl, alkynyl, where examples relating to bridges suitable with preference are shown above.

According to the invention, the $Y^3$ radical in the structures a, b, c, d and e is hydrogen, an alkyl, alkynyl or alkenyl radical, preferred alkyl, alkynyl and alkenyl radicals having been specified above, more preferably an alkyl radical, most preferably methyl, ethyl, isopropyl, n-propyl, n-butyl, isobutyl or tert-butyl, especially preferably methyl or isopropyl; or

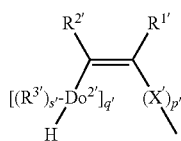

where $Do^{2'}$, q', s', $R^{3'}$, $R^{1'}$, $R^{2'}$, X' and p' are each independently as defined for $Do^2$, q, s, $R^3$, $R^1$, $R^2$, X and p—which have already been defined above;

$Y^3$ in the structures a, b, c, d and e is preferably an alkyl, alkynyl or alkenyl radical, preferred alkyl, alkynyl and alkenyl radicals having been specified above, more preferably an alkyl radical, most preferably methyl, ethyl, isopropyl, n-propyl, n-butyl, isobutyl or tert-butyl, especially preferably methyl or isopropyl.

The moiety

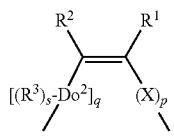

of the carbene ligand of the formula II preferably has the structure

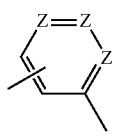

in which the symbols are each defined as follows:

Z are each independently $CR^{12}$ or N, where from 0 to 3 of the Z symbols may be N, preferably from 0 to 2, more preferably 0 or 1, and Z, in the case that one symbol Z is N, may be arranged in the o-, m- or p-position, preferably in the o- or p-position, to the bonding site of the moiety with the moiety

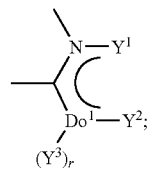

$R^{12}$ in the Z groups are each independently H, an alkyl, aryl, heteroaryl, alkynyl, alkenyl radical, or in each case 2 $R^{12}$ radicals together form a fused ring which may optionally comprise at least one heteroatom, preferably N, or $R^{12}$ is a radical with donor or acceptor action; preferably H or a radical with donor or acceptor action;

in addition, the group of the structure

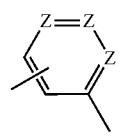

via the aromatic base structure or via one of the $R^{12}$ radicals, may be bonded to $Y^1$ via a bridge, where the bridge may be defined as follows:

alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;

and $R^{18}$, $R^{19}$, $R^{20}$, $R^{21}$, $R^{22}$, $R^{30}$, $R^{31}$ are each H, alkyl, aryl, heteroaryl, alkenyl, alkynyl.

In a preferred embodiment of the present invention, the group

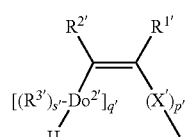

in the symmetrical carbene ligands is defined as follows:

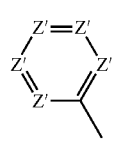

in which the symbols are each defined as follows:

Z' are each independently $CR^{12'}$ or N, where from 0 to 5 of the symbols Z' may each be N, preferably from 0 to 4, more preferably from 0 to 3, most preferably from 0 to 2, especially preferably 0 or 1, and Z', in the case that 1 symbol Z' is N, may be arranged in the o-, m- or p-position, preferably in the o- or p-position, to the bonding site of the moiety with the moiety

[structure with R², R¹, [(R³)ₛ-Do²]_q, (X)_p, N—Y¹, Do¹—Y², (Y³)_r]

$R^{12'}$ in the Z' groups are each independently H, an alkyl, aryl, heteroaryl, alkynyl, alkenyl radical, or in each case 2 $R^{12'}$ radicals together form a fused ring which may optionally comprise at least one heteroatom, preferably N, or $R^{12'}$ is a radical with donor or acceptor action; preferably H or a radical with donor or acceptor action;

in addition, the group of the structure

[structure with Z'=Z', Z', Z', Z']

via the aromatic base structure or via one of the $R^{12'}$ radicals, may be bonded to $Y^1$ via a bridge, where the bridge may be defined as follows:

alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;

and $R^{18}$, $R^{19}$, $R^{20}$, $R^{21}$, $R^{22}$, $R^{30}$, $R^{31}$ are each H, alkyl, aryl, heteroaryl, alkenyl, alkynyl.

In addition, $Y^3$ and $Y^2$ in each of the n carbene ligands of the general formula II may be bonded to one another via a bridge, where the bridge may be defined as follows:

alkylene, arylene, heteroarylene, alkynylene, alkenylene, $NR^{25}$, $PR^{26}$, $BR^{27}$, O, S, SO, $SO_2$, $SiR^{32}R^{33}$, CO, CO—O, O—CO and $(CR^{28}R^{29})_y$, where one or more nonadjacent $(CR^{28}R^{29})$ groups may be replaced by $NR^{25}$, $PR^{26}$, $BR^{27}$, O, S, SO, $SO_2$, $SiR^{32}R^{33}$, CO, CO—O, O—CO, where y is from 2 to 10;

and $R^{25}$, $R^{26}$, $R^{27}$, $R^{28}$, $R^{29}$, $R^{32}$, $R^{33}$ are each H, alkyl, aryl, heteroaryl, alkenyl, alkynyl.

In a very particularly preferred embodiment, the present invention relates to heteroleptic carbene complexes of the formula I in which the at least one carbene ligand is selected from the group consisting of aa ab ac ad ae where the symbols are each defined as follows:

$Y^3$ is an alkyl, alkynyl or alkenyl radical or
a group of the following structure

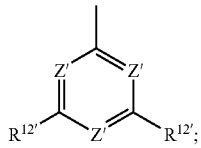

Z is the same or different and is $CR^{12}$ or N;
Z' is the same or different and is $CR^{12'}$ or N;
Z" is the same or different and is $CR^{10}$ or N;
$R^{12}, R^{12'}$ are the same or different and are each independently H, an alkyl, aryl, heteroaryl, alkynyl or alkenyl radical, or in each case 2 $R^{12}$ or $R^{12'}$ radicals together form a fused ring which may optionally comprise at least one heteroatom, or $R^{12}$ or $R^{12'}$ is a radical with donor or acceptor action;
$R^4, R^5, R^6, R^7, R^8, R^9, R^{11}$ and $R^{11'}$ are each hydrogen, alkyl, aryl, heteroaryl, alkynyl or alkenyl, or a radical with donor or acceptor action;
$R^{10}$ in the Z" groups are each independently H, alkyl, aryl, heteroaryl, alkynyl or alkenyl, or in each case 2 $R^{10}$ radicals together form a fused ring which may optionally comprise at least one heteroatom, or $R^{10}$ is a radical with donor or acceptor action;
in addition, the group of the structure

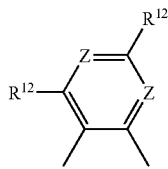

via the aromatic base structure or via one of the $R^{12}$ radicals, may be bonded via a bridge to $R^4$ or $R^5$ or the carbon atom to which $R^4$ and $R^5$ are bonded in the moiety aa, $R^8$ or the carbon atom to which $R^8$ is bonded in the moiety ab, one of the $R^{10}$ radicals or one of the carbon atoms to which $R^{10}$ is bonded in the moiety ac, and $R^{11}$ or the carbon atom to which $R^{11}$ is bonded in the moiety ad;
and/or
the group of the structure

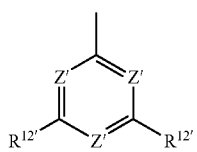

via the aromatic base structure or via one of the $R^{12'}$ radicals, may be bonded via a bridge to $R^6$ or $R^7$ or the carbon atom to which $R^6$ and $R^7$ are bonded in the moiety aa, $R^9$ or the carbon atom to which $R^9$ is bonded in the moiety ab, one of the $R^{10}$ radicals or one of the carbon atoms to which $R^{10}$ is bonded in the moiety ac, and $R^{11'}$ or the carbon atom to which $R^{11'}$ is bonded in the moiety ae;
where the particular bridge may be defined as follows:
alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;
and
$R^{18}, R^{19}, R^{20}, R^{21}, R^{22}, R^{30}, R^{31}$
are each H, alkyl, aryl, heteroaryl, alkenyl, alkynyl;
where, in the cases in which the group of the structure

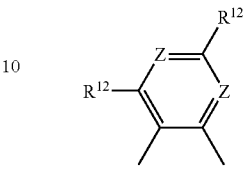

is bonded via a bridge to the carbon atom to which $R^4$ and $R^5$ are bonded (moiety aa), the carbon atom to which $R^8$ is bonded (moiety ab), one of the carbon atoms to which $R^{10}$ is bonded (moiety ac) or the carbon atom to which $R^{11}$ is bonded (moiety ad), the particular $R^4$ or $R^5$ radical, $R^8$, one of the $R^{10}$ radicals or $R^{11}$ is replaced by a bond to the bridge;
and, in the cases in which the group of the structure

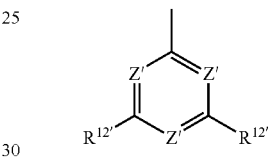

is bonded via a bridge to the carbon atom to which $R^6$ and $R^7$ are bonded (moiety aa), the carbon atom to which $R^9$ is bonded (moiety ab), one of the carbon atoms to which $R^{10}$ is bonded (moiety ac) or the carbon atom to which $R^{11'}$ is bonded (moiety ad), the particular $R^6$ or $R^7$ radical, $R^9$, one of the $R^{10}$ radicals or $R^{11'}$ is replaced by a bond to the bridge.

More preferably, $Y^3$ in the structures aa, ab, ac, ad and ae is an alkyl, alkynyl or alkenyl radical, preferred alkyl, alkynyl or alkenyl radicals having been mentioned above.

The carbene ligand of the formula II, in a preferred embodiment of the present invention, is thus an "unsymmetrical" carbene ligand in which $Y^3$ is hydrogen, an alkyl, alkynyl or alkenyl radical, preferably an alkyl, alkynyl or alkenyl radical, preferred alkyl, alkynyl or alkenyl radicals having been mentioned above.

If further carbene ligands are present in the inventive heteroleptic carbene complexes (when n in the carbene complexes of the formula I is $\geq 2$), they may be identical to the first carbene ligand or different from the first carbene ligand. In the case of $n \geq 2$, the carbene ligands are preferably identical. In the case that the carbene ligands are different, it is possible, for example, for one carbene ligand to be "unsymmetrical", i.e. $Y^3$ is: hydrogen, an alkyl, alkynyl or alkenyl radical, preferably an alkyl, alkynyl or alkenyl radical, and for a further carbene ligand to be "symmetrical", i.e. $Y^3$ is:

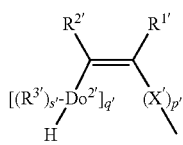

where Do²', q', s', R³', R¹', R²', X' and p' have been defined above. It is also possible that the heteroleptic carbene complex of the formula I has a plurality of different symmetrical carbene ligands or a plurality of different unsymmetrical carbene ligands.

According to the invention, the heteroleptic carbene complexes of the general formula I of the present application comprise, in addition to at least one carbene ligand of the general formula II, at least one heterocyclic noncarbene ligand (het) of the general formula III:

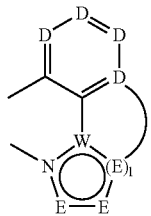

(III)

in which the symbols in the het ligand of the general formula III are each defined as follows:

D are each independently $CR^{34}$ or N; preferably $CR^{34}$;
W is C, N, P; preferably C or N;
E are each independently $CR^{35}$, N, $NR^{36}$, S, O, P or $PR^{37}$; preferably each independently $CR^{35}$, N, $NR^{36}$, S or O;
l is 1 or 2;
$R^{34}, R^{35}, R^{36}, R^{37}$
are each independently H, an alkyl, aryl, heteroaryl, alkynyl or alkenyl radical, or in each case 2 $R^{34}, R^{35}, R^{36}$ or $R^{37}$ radicals together form a fused ring which may optionally comprise at least one heteroatom, or $R^{34}, R^{35}, R^{36}$ or $R^{37}$ is a radical with donor or acceptor action;

where the dotted line means an optional bridge between one of the D groups and one of the E groups; where the bridge may be defined as follows:

alkylene, arylene, heteroarylene, alkynylene, alkenylene, $NR^{38}$, $PR^{39}$, $BR^{40}$, O, S, SO, $SO_2$, $SiR^{41}R^{42}$, CO, CO—O, O—CO and $(CR^{43}R^{44})_v$, where one or more nonadjacent $(CR^{43}R^{44})$ groups may be replaced by $NR^{38}$, $PR^{39}$, $BR^{40}$, O, S, SO, $SO_2$, $SiR^{41}R^{42}$, CO, CO—O, O—CO, where
v is from 2 to 10;
and
$R^{38}, R^{39}, R^{40}, R^{41}, R^{42}, R^{43}, R^{44}$
are each H, alkyl, aryl, heteroaryl, alkenyl, alkynyl.

Very particular preference is given to ligands of the general formula III which, in addition to their nitrogen atom, have 0, 1 or 2 heteroatoms, preferably selected from N, O and S.

Very especially preferably, the heterocyclic noncarbene ligands of the general formula III have the following structures ba to bu:

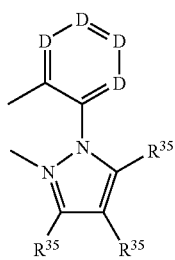

ba

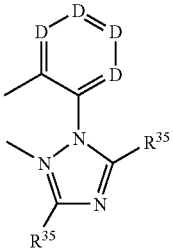

bb

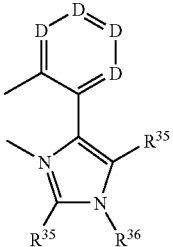

bc

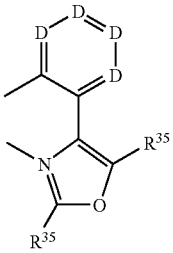

bd

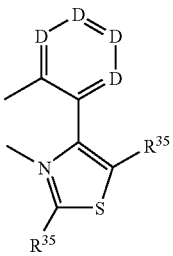

be

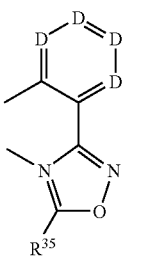

bf

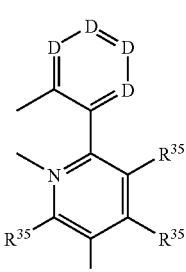

bg bh 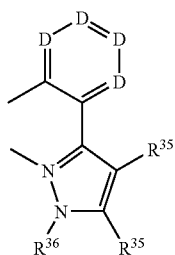
bi 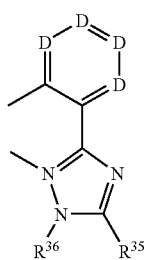
bj 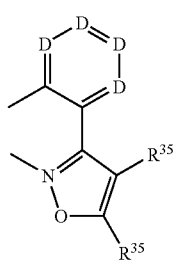
bk 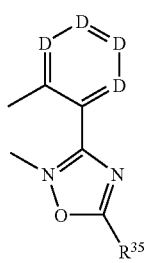
bl 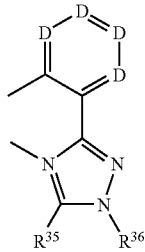
bm 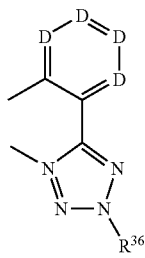
bn 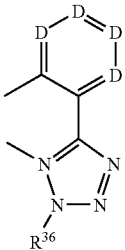
bo 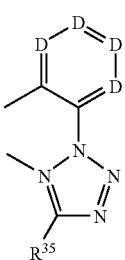
bp 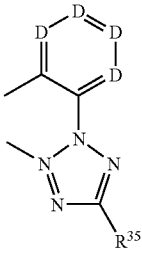
bq 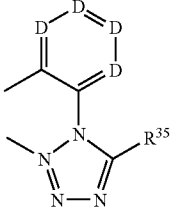
br 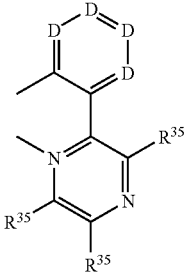
bs 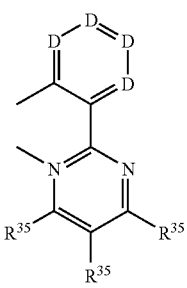

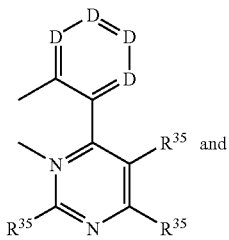
bt

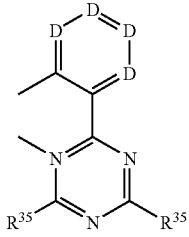
bu in which:
D are each independently CR$^{34}$ or N; preferably, from 0 to 3 D groups are each N, more preferably from 0 to 2, most preferably 0, 1 or 2, where the further D groups are each CR$^{34}$; very especially preferably, D in the structures ba to bu is CR$^{34}$;

R$^{34}$, R$^{35}$, R$^{36}$
are each independently H, an alkyl, aryl, heteroaryl, alkynyl or alkenyl radical, or in each case 2 R$^{34}$, R$^{35}$ or R$^{36}$ radicals together form a fused ring which may optionally comprise at least one heteroatom, or R$^{34}$, R$^{35}$ or R$^{36}$ is a radical with donor or acceptor action; preferably, H, an alkyl or aryl radical or a radical with donor or acceptor action.

The metal atom M$^1$ in the inventive heteroleptic carbene complexes of the general formula I is more preferably selected from the group consisting of Ir, Os, Rh and Pt, preference being given to Os(II), Rh(III), Ir(III) and Pt(II). Particular preference is given to Ir(III).

In a further preferred embodiment, the metal atom M$^1$ is Fe(II), Fe(III), Ru(II), Cr(III), Mo(VI), W(0), Re(II), Mn(II), Ir(III), Co(II), Co(III), Rh(III), Os(II), Pt(IV), n=2 and m=1. Very particular preference is given to heteroleptic carbene complexes in which M$^1$ is Ir(III), n=2 and m=1. These inventive heteroleptic carbene complexes, compared to heteroleptic carbene complexes which exhibit the same ligands but in which n=1 and m=2, are notable for a significantly improved efficiency.

In a very particularly preferred embodiment, the inventive heteroleptic carbene complexes thus have the formula (Ii):

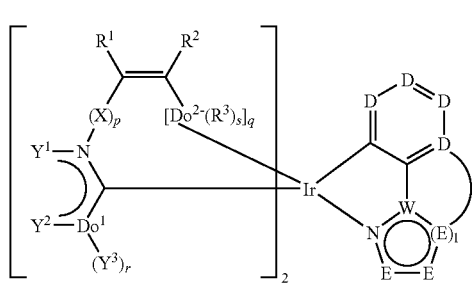
(Ii)

where the symbols in the carbene complexes of the general formula (Ii) are each defined as follows:
Do$^1$ is a donor atom selected from the group consisting of C, P, N, O, S and Si, preferably P, N, O and S;
Do$^2$ is a donor atom selected from the group consisting of C, N, P, O and S;
r is 2 when Do$^1$ is C or Si, is 1 when Do$^1$ is N or P, and is 0 when Do$^1$ is O or S;
s is 2 when Do$^2$ is C, is 1 when Do$^2$ is N or P, and is 0 when Do$^2$ is O or S;
X is a spacer selected from the group consisting of silylene, alkylene, arylene, heteroarylene, alkynylene, alkenylene, NR$^{13}$, PR$^{14}$, BR$^{15}$, O, S, SO, SO$_2$, CO, CO—O, O—CO and (CR$^{16}$R$^{17}$)$_w$, where one or more nonadjacent (CR$^{16}$R$^{17}$) groups may be replaced by NR$^{13}$, PR$^{14}$, BR$^{15}$, O, S, SO, SO$_2$, CO, CO—O, O—CO;
w is from 2 to 10;
R$^{13}$, R$^{14}$, R$^{15}$, R$^{16}$, R$^{17}$ are each
H, alkyl, aryl, heteroaryl, alkenyl, alkynyl;
p is 0 or 1;
q is 0 or 1;
Y$^1$, Y$^2$ are each independently hydrogen or a carbon group selected from the group consisting of alkyl, aryl, heteroaryl, alkynyl and alkenyl groups;
or
Y$^1$ and Y$^2$ together form a bridge between the donor atom Do$^1$ and the nitrogen atom N, said bridge having at least two atoms of which at least one is a carbon atom,
R$^1$, R$^2$ are each independently hydrogen, alkyl, aryl, heteroaryl, alkynyl or alkenyl radicals,
or
R$^1$ and R$^2$ together form a bridge having a total of from three to five atoms, of which from 1 to 5 atoms may be heteroatoms and the remaining atoms are carbon atoms, so that the group

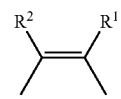

forms a five- to seven-membered ring which, if appropriate— in addition to the double bond already present—may have one further double bond or—in the case of a six- or seven-membered ring—two further double bonds, and may optionally be substituted by alkyl or aryl groups and/or groups with donor or acceptor action, and may optionally comprise at least one heteroatom, and the five- to seven-membered ring may optionally be fused to one or more further rings;
in addition, Y$^1$ and R$^1$ may be bonded to one another via a bridge, where the bridge may be defined as follows:
alkylene, arylene, heteroarylene, alkynylene, alkenylene, NR$^{18}$, PR$^{19}$, BR$^{20}$, O, S, SO, SO$_2$, SiR$^{30}$R$^{31}$, CO, CO—O, O—CO and (CR$^{21}$R$^{22}$)$_x$, where one or more nonadjacent (CR$^{21}$R$^{22}$) groups may be replaced by NR$^{18}$, PR$^{19}$, BR$^{20}$, O, S, SO, SO$_2$, SiR$^{30}$R$^{31}$, CO, CO—O, O—CO, where
x is from 2 to 10;
and
R$^{18}$, R$^{19}$, R$^{20}$, R$^{21}$, R$^{22}$, R$^{30}$, R$^{31}$
are each H, alkyl, aryl, heteroaryl, alkenyl, alkynyl;
R$^3$ is hydrogen, an alkyl, aryl, heteroaryl, alkynyl or alkenyl radical;

$Y^3$ is hydrogen, an alkyl, alkynyl or alkenyl radical,
or

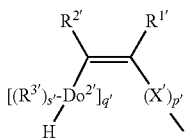

where $Do^{2'}$, $q'$, $s'$, $R^{3'}$, $R^{1'}$, $R^{2'}$, $X'$ and $p$ are each independently as defined for $Do^2$, $q$, $s$, $R^3$, $R^1$, $R^2$, $X$ and $p$;
in addition, $Y^3$ and $Y^2$ in each of the n carbene ligands may be bonded to one another via a bridge, where the bridge may be defined as follows:
alkylene, arylene, heteroarylene, alkynylene, alkenylene, $NR^{25}$, $PR^{26}$, $BR^{27}$, O, S, SO, $SO_2$, $SiR^{32}R^{33}$, CO, CO—O, O—CO and $(CR^{28}R^{29})_y$, where one or more nonadjacent $(CR^{28}R^{29})$ groups may be replaced by $NR^{25}$, $PR^{26}$, $BR^{27}$, O, S, SO, $SO_2$, $SiR^{32}R^{33}$, CO, CO—O, O—CO, where
y is from 2 to 10;
and
$R^{25}$, $R^{26}$, $R^{27}$, $R^{28}$, $R^{29}$, $R^{32}$, $R^{33}$
are each H, alkyl, aryl, heteroaryl, alkenyl, alkynyl;
D are each independently $CR^{34}$ or N;
W is C, N, P;
E are each independently $CR^{35}$, N, $NR^{36}$, S, O, P or $PR^{37}$;
I is 1 or 2;
$R^{34}$, $R^{35}$, $R^{36}$, $R^{37}$
are each independently H, an alkyl, aryl, heteroaryl, alkynyl or alkenyl radical, or in each case 2 $R^{34}$, $R^{35}$, $R^{36}$ or $R^{37}$ radicals together form a fused ring which may optionally comprise at least one heteroatom, or $R^{34}$, $R^{35}$, $R^{36}$ or $R^{37}$ is a radical with donor or acceptor action;
where the radicals, groups and indices $R^1$, $R^2$, $R^3$, $Do^1$, $Do^2$, $Y^1$, $Y^2$, $Y^3$, X, p, q and r in the carbene ligands in the compounds of the general formula Ii may be the same or different; where the dotted line is an optional bridge between one of the D groups and one of the E groups; where the bridge may be defined as follows:
alkylene, arylene, heteroarylene, alkynylene, alkenylene, $NR^{38}$, $PR^{39}$, $BR^{40}$, O, S, SO, $SO_2$, $SiR^{41}R^{42}$, CO, CO—O, O—CO and $(CR^{43}R^{44})_v$, where one or more nonadjacent $(CR^{43}R^{44})$ groups may be replaced by $NR^{38}$, $PR^{39}$, $BR^{40}$, O, S, SO, $SO_2$, $SiR^{41}R^{42}$, CO, CO—O, O—CO, where
v is from 2 to 10;
and
$R^{38}$, $R^{39}$, $R^{40}$, $R^{41}$, $R^{42}$, $R^{43}$, $R^{44}$
are each H, alkyl, aryl, heteroaryl, alkenyl, alkynyl.

Preferred embodiments and definitions of the radicals, groups and indices specified in the general formula Ii correspond to the definitions already specified above for these radicals, groups and indices.

The inventive heteroleptic carbene complexes of the formula I can in principle be prepared analogously to processes known to those skilled in the art, taking into account the fact that the inventive heteroleptic carbene complexes of the formula I bear at least one carbene ligand of the general formula II and at least one heterocyclic noncarbene ligand of the general formula III. Suitable processes for preparing carbene complexes are detailed, for example, in the review articles W. A. Hermann et al., Advances in Organometallic Chemistry, 2001 vol. 48, 1 to 69, W. A. Hermann et al., Angew. Chem. 1997, 109, 2256 to 2282 and G. Bertrand et al. Chem. Rev. 2000, 100, 39 to 91 and the literature cited therein, and also in WO 2005/113704, WO 2005/019373 and in European application EP 06 101 109.4 which had not been published at the priority date of the present application.

In one embodiment, the inventive heteroleptic carbene complexes of the formula I are prepared from ligand precursors corresponding to the carbene ligands, the heterocyclic noncarbene ligands and suitable metal complexes comprising the desired metal.

Suitable ligand precursors of the carbene ligands are known to those skilled in the art. They are preferably cationic precursors of the carbene ligands of the general formula IV

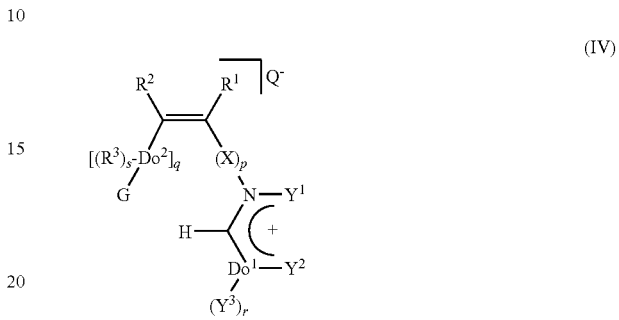

in which
$Q^-$ is a monoanionic counterion, preferably halide, pseudohalide, $BF_4^-$, $BPh_4^-$, $PF_6^-$, $AsF_6^-$ or $SbF_6^-$;
and
G is H when $Do^2$=C or q=0, and
  is H or is a free electron pair of the heteroatom when $Do^2$=N, S, O or P; and
the further radicals, symbols and indices in the ligand precursor of the general formula IV are each as defined above.

The ligand precursors of the general formula IV may be prepared by processes known to those skilled in the art. Suitable processes are mentioned, for example, in WO 2005/019373 and the literature cited therein, for example Organic Letters, 1999, 1, 953-956; Angewandte Chemie, 2000, 112, 1672-1674. Further suitable processes are mentioned, for example, in T. Weskamp et al., J. Organometal. Chem. 2000, 600, 12-22; G. Xu et al., Org. Lett. 2005, 7, 4605-4608; V. Lavallo et al., Angew. Chem. Int. Ed. 2005, 44, 5705-5709. Some of the suitable ligand precursors are commercially available.

Suitable heterocyclic noncarbene ligand precursors are likewise known to those skilled in the art. The ligand precursors are preferably of the general formula V

In which:
D are each independently $CR^{34}$ or N;
W is C, N, P;
E are each independently $CR^{35}$, N, $NR^{36}$, S, O, P or $PR^{37}$;
I is 1 or 2;
$R^{34}$, $R^{35}$, $R^{36}$, $R^{37}$ are each independently H, an alkyl, aryl, heteroaryl, alkynyl or alkenyl radical, or in each case 2 $R^{34}$, $R^{35}$, $R^{36}$ or $R^{37}$ radicals together form a fused ring which may optionally comprise at least one heteroatom, or $R^{34}$, $R^{35}$, $R^{36}$ or $R^{37}$ is a radical with donor or acceptor action; where the dotted line means an optional bridge between one of the D groups and one of the E groups; where the bridge may be defined as follows: alkylene, arylene, heteroarylene, alkynylene, alkenylene, $NR^{38}$, $PR^{39}$, $BR^{40}$, O, S, SO, $SO_2$, $SiR^{41}R^{42}$, CO, CO—O, O—CO and $(CR^{43}R^{44})_v$, where one or more nonadjacent $(CR^{43}R^{44})$ groups may be replaced by $NR^{38}$, $PR^{39}$, $BR^{40}$, O, S, SO, $SO_2$, $SiR^{41}R^{42}$, CO, CO—O, O—CO, where v is from 2 to 10;
and
$R^{38}$, $R^{39}$, $R^{40}$, $R^{41}$, $R^{42}$, $R^{43}$, $R^{44}$
are each H, alkyl, aryl, heteroaryl, alkenyl, alkynyl.

Preferred embodiments of the radicals, symbols and indices specified have been specified above.

The ligand precursors of the general formula V can be prepared by processes known to those skilled in the art or are commercially available. Suitable preparation processes are disclosed, for example, in B. M Choudary et al., *J. Am. Chem. Soc.* 2005, 127, 9948; H. Zhang et al., *J. Org. Chem.* 2005, 70, 5164; S. V. Ley et al., *Angew. Chem. Int. Ed.* 2003, 42, 5400; J. Hassan et al., *Chem. Rev.* 2002, 102, 1359; *Metal-catalyzed Cross-coupling Reactions*, A. de Meijere, F. Diederich, Wiley-VCH, 2004.

In a preferred embodiment, the present invention relates to a process for preparing the inventive heteroleptic carbene complexes of the general formula I, the preparation comprising the following step:

reacting at least one ligand precursor of the general formula (IV)

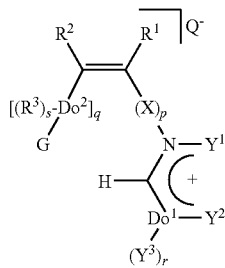

(IV)

in which the symbols, radicals and indices are each as defined above;
and
at least one ligand precursor of the general formula V

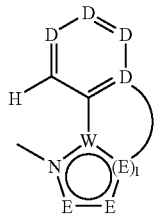

(V)

in which the symbols, radicals and indices are each as defined above;
with a metal complex comprising at least one metal $M^{1'}$, where $M^{1'}$ is defined as follows:

$M^{1'}$ is a metal atom selected from the group consisting of Ir, Co, Rh, Ni, Pd, Pt, Fe, Ru, Os, Cr, Mo, W, Mn, Tc, Re, Cu and Au, preferably Ir, Os, Ru, Rh, Pd, Co and Pt, more preferably Ir, Pt, Rh and Os, in any oxidation state possible for the corresponding metal atom.

The preparation of the inventive heteroleptic carbene complexes is in principle possible by simultaneous reaction of carbene ligand precursors of the general formula IV and ligand precursors of the general formula V with a metal complex comprising at least one metal $M^{1'}$ ("one-pot process") or preferably by sequential reaction. The sequential reaction can be effected either by reacting the metal complex with at least one carbene ligand precursor of the general formula IV in a first step wherein, as an intermediate, a carbene complex which has at least one carbene ligand either of the general formula II or as the non-cyclometalated form, and at least one further coordination means (where the further coordination means is present either by virtue of a free coordination site on the metal $M^{1'}$ or by virtue of the displacement of other ligands) for at least one further bidentate heterocyclic noncarbene ligand of the formula III is formed; or by reacting the metal complex with at least one ligand precursor of the general formula V in a first step wherein, as an intermediate, a complex which has at least one heterocyclic noncarbene ligand either of the general formula III or as the non-cyclometalated form, and at least one further coordination means (where the further coordination means is present either by virtue of a free coordination site on the metal $M^{1'}$ or by virtue of the displacement of other ligands) for at least one bidentate carbene ligand of the formula II is formed. In a second step which follows the first step, the particular complex obtained in the first step is reacted with at least one ligand precursor of the general formula V (when at least one carbene ligand precursor of the general formula IV has been used in the first step) or with at least one carbene ligand precursor of the general formula IV (when at least one ligand precursor of the general formula V has been used in the first step).

In the particularly preferred case that the metal $M^1$ in the inventive heteroleptic carbene complexes of the formula I is Ir(III) with a coordination number of 6, a sequential reaction gives rise, for example, to the following particularly preferred routes to obtain a carbene complex of the general formula Ii:

Route ia:
(iaa) Reaction of a metal complex comprising at least one metal $M^{1'}$ in which the at least one metal $M^{1'}$ is Ir with at least double the stoichiometric amount, in relation to Ir, of a carbene ligand precursor IV to form a dicarbene complex which has carbene ligands of the general formula II and a further coordination site for a further bidentate ligand, and
(iab) subsequent reaction of the resulting dicarbene complex with an at least stoichiometric amount, in relation to Ir, of a ligand precursor of the general formula V to obtain a heteroleptic Ir-carbene complex of the general formula Ii.

Route ib:
(iba) Reaction of a metal complex comprising at least one metal $M^{1'}$ in which the at least one metal $M^{1'}$ is Ir with an at least stoichiometric amount, in relation to Ir, of a ligand precursor of the general formula V to form a complex which has a heterocyclic noncarbene ligand of the general formula III and two further coordination sites for two further bidentate ligands, and
(ibb) subsequent reaction of the resulting complex with at least double the stoichiometric amount, in relation to Ir, of a carbene ligand precursor of the general formula IV to obtain a heteroleptic Ir-carbene complex of the general formula Ii.

In the intermediates formed in steps (iaa) and (iba), the particular carbene ligands and noncarbene ligands may be present either in cyclometalated form or in non-cyclometalated form.

In a particularly preferred embodiment of the present invention, the reaction to give a carbene complex of the general formula Ii is effected according to route ia.

The aforementioned complexes obtained in step (iaa) or (iba) can, if appropriate, be isolated or be reacted with the further ligand precursor(s) "in situ", i.e. without workup.

The metal complex comprising at least one metal $M^{1'}$ is a metal complex comprising at least one metal selected from the group consisting of Ir, Co, Rh, Ni, Pd, Pt, Fe, Ru, Os, Cr, Mo, W, Mn, Tc, Re, Cu and Au, preferably Ir, Os, Ru, Rh, Pd, Co and Pt, more preferably Ir, Pt, Rh and Os, most preferably Ir, in any oxidation state possible for the corresponding metal atom, preferably Ir(I) or Ir(III). Suitable metal complexes are known to those skilled in the art. Examples of suitable metal complexes are $Pt(cod)Cl_2$, $Pt(cod)Me_2$, $Pt(acac)_2$, $Pt(PPh_3)_2Cl_2$, $PtCl_2$, $[Rh(cod)Cl]_2$, $Rh(acac)CO(PPh_3)$, $Rh(acac)(CO)_2$, $Rh(cod)_2BF_4$, $RhCl(PPh_3)_3$, $RhCl_3$ n $H_2O$, $Rh(acac)_3$, $[Os(CO)_3I_2]_2$, $[Os_3(CO)_{12}]$, $OsH_4(PPh_3)_3$, $Cp_2Os$, $Cp^*_2Os$, $H_2OsCl_6 \cdot 6H_2O$, $OsC_3 \cdot H_2O$), and $[(\mu-Cl)Ir(\eta^4-1,5-cod)]_2$, $[(\mu-Cl)Ir(\eta^2-coe)_2]_2$, $Ir(acac)_3$, $IrCl_3 \cdot nH_2O$, $(tht)_3IrCl_3$, $Ir(\eta^3-allyl)_3$, $Ir(\eta^3-methallyl)_3$, in which cod is cyclooctadiene, coe is cyclooctene, acac is acetylacetonate and tht is tetrahydrothiophene. The metal complexes can be prepared by processes known to those skilled in the art or are commercially available.

In the preparation of iridium(III) complexes of the general formula I ($M^1$ in formula I is Ir), which are particularly preferred in the present application, the aforementioned iridium (I) or (III) complexes can be used, especially $[(\mu-Cl)Ir(\eta^4-1,5-cod)]_2$, $[(\mu-Cl)Ir(\eta^2-coe)_2]_2$, $Ir(acac)_3$, $IrCl_3 \cdot nH_2O$, $(tht)_3IrCl_3$, $Ir(\eta^3-allyl)_3$, $Ir(\eta^3-methallyl)_3$, in which cod is cyclooctadiene, coe is cyclooctene, acac is acetylacetonate and tht is tetrahydrothiophene.

After the reaction, the inventive heteroleptic carbene complex is worked up and, if appropriate, purified by processes known to those skilled in the art. Typically, the workup and purification are effected by extraction, column chromatography and/or recrystallization by processes known to those skilled in the art.

The inventive heteroleptic carbene complexes are outstandingly suitable as emitter substances, since they have an emission (electroluminescence) in the visible region of the electromagnetic spectrum. With the aid of the inventive heteroleptic carbene complexes as emitter substances, it is possible to provide compounds which exhibit electroluminescence in the red, green and in the blue region of the electromagnetic spectrum with very good efficiency. At the same time, the quantum yield is high and the stability of the inventive heteroleptic carbene complexes in the device is high.

In addition, the inventive heteroleptic carbene complexes are suitable as electron, exciton or hole blockers, or hole conductors, electron conductors, hole injection layer or matrix material in OLEDs, depending on the ligands used and the central metal used.

Organic light-emitting diodes (OLEDs) are in principle composed of several layers:
1. Anode (1)
2. Hole-transporting layer (2)
3. Light-emitting layer (3)
4. Electron-transporting layer (4)
5. Cathode (5)

However, it is also possible that the OLED does not have all of the layers mentioned; for example an OLED having the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5), or the layers (1), (3), (4) and (5), are likewise suitable.

The heteroleptic carbene complexes according to the present application may be used in various layers of an OLED. The present invention therefore further provides for the use of the inventive heteroleptic carbene complexes in organic light-emitting diodes (OLEDs), and also an OLED comprising at least one inventive heteroleptic carbene complex. The inventive heteroleptic carbene complexes are used preferably in the light-emitting layer, more preferably as emitter molecules. The present invention therefore further provides a light-emitting layer comprising at least one heteroleptic carbene complex, preferably as an emitter molecule. Preferred heteroleptic carbene complexes have been specified above.

The inventive heteroleptic carbene complexes may be present in bulk—without further additives—in the light-emitting layer or another layer of the OLED, preferably in the light-emitting layer. However, it is likewise possible and preferred that, in addition to the inventive heteroleptic carbene complexes, further compounds are present in the layers comprising at least one inventive heteroleptic carbene complex, preferably in the light-emitting layer. For example, a fluorescent dye may be present in the light-emitting layer in order to alter the emission color of the heteroleptic carbene complex used as an emitter molecule. In addition—in a preferred embodiment—a diluent material may be used. This diluent material may be a polymer, for example poly(N-vinylcarbazole) or polysilane. However, the diluent material may likewise be a small molecule, for example 4,4'-N,N'-dicarbazolebiphenyl (CDP=CBP) or tertiary aromatic amines.

The individual aforementioned layers of the OLED may in turn be composed of 2 or more layers. For example, the hole-transporting layer may be composed of one layer into which holes are injected from the electrode and one layer which transports the holes from the hole injection layer away into the light-emitting layer. The electron-transporting layer may likewise consist of a plurality of layers, for example one layer in which electrons are injected by the electrode and one layer which receives electrons from the electron injection layer and transports them into the light-emitting layer. These specified layers are each selected according to factors such as energy level, thermal resistance and charge carrier mobility, and also energy differential of the layers mentioned with the organic layers or the metal electrodes. Those skilled in the art are capable of selecting the structure of the OLEDs in such a way that it is adapted optimally to the heteroleptic carbene complexes used in accordance with the invention, preferably as emitter substances.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer should be aligned to the work function of the cathode.

The present application further provides an OLED comprising at least one inventive light-emitting layer. The further layers in the OLED may be composed of any material which is typically used in such layers and is known to those skilled in the art.

The anode (1) is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed.

Suitable hole-transporting materials for the layer (2) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole-transporting material. Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde-diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)triphenylamine (TDTA) and porphyrin compounds, and also phthalocyanines such as copper phthalocyanines. Customarily used hole-transporting polymers are selected from the group consisting of polyvinylcarbazoles, (phenylmethyl)polysilanes, PEDOT (poly(3,4-ethylenedioxythiophene)), preferably PEDOT doped with PSS (polystyrenesulfonate), and polyanilines. It is likewise possible to obtain hole-transporting polymers by doping hole-transporting molecules into polymers such as polystyrene and polycarbonate.

Suitable hole-transporting molecules are the molecules already mentioned above.

Suitable electron-transporting materials for the layer (4) of the inventive OLEDs comprise metals chelated with oxinoid compounds, such as tris(8-hydroxyquinolinolato)aluminum ($Alq_3$), compounds based on phenanthroline such as 2,9-dimethyl-4,7-diphenyl-1,10-phenanthroline (DDPA=BCP) or 4,7-diphenyl-1,10-phenanthroline (DPA) and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). The layer (4) may serve both to ease the electron transport and as a buffer layer or as a barrier layer in order to prevent quenching of the exciton at the interfaces of the layers of the OLED. The layer (4) preferably improves the mobility of the electrons and reduces quenching of the exciton.

Of the materials specified above as hole-transporting materials and electron-transporting materials, some can fulfill a plurality of functions. For example, some of the electron-conducting materials are simultaneously hole-blocking materials when they have a low-lying HOMO.

The charge transport layers may also be electronically doped in order to improve the transport properties of the materials used, in order firstly to make the layer thicknesses more generous (avoidance of pinholes/short circuits) and secondly to minimize the operating voltage of the device. For example, the hole-transporting materials may be doped with electron acceptors; for example, phthalocyanines or arylamines such as TPD or TDTA may be doped with tetrafluorotetracyanoquinodimethane (F4-TCNQ). The electron-transporting materials may, for example, be doped with alkali metals, for example $Alq_3$ with lithium. Electronic doping is known to those skilled in the art and is disclosed, for example, in W. Gao, A. Kahn, J. Appl. Phys., Vol. 94, No. 1, Jul. 1, 2003 (p-doped organic layers); A. G. Werner, F. Li, K. Harada, M. Pfeiffer, T. Fritz, K. Leo, Appl. Phys. Lett., Vol. 82, No. 25, Jun. 23, 2003 and Pfeiffer et al., Organic Electronics 2003, 4, 89-103.

The cathode (5) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used. In addition, lithium-comprising organometallic compounds or LiF may be applied between the organic layer and the cathode in order to reduce the operating voltage.

The OLED of the present invention may additionally comprise further layers which are known to those skilled in the art. For example, a layer which eases the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may serve as a protective layer.

In a preferred embodiment, the inventive OLED, in addition to the layers (1) to (5), comprises at least one of the further layers mentioned below:

a hole injection layer between the anode (1) and the hole-transporting layer (2);
  a blocking layer for electrons and/or excitons between the hole-transporting layer (2) and the light-emitting layer (3);
  a blocking layer for holes and/or excitons between the light-emitting layer (3) and the electron-transporting layer (4);
  an electron injection layer between the electron-transporting layer (4) and the cathode (5).

As already mentioned above, it is, however, also possible that the OLED does not have all of the layers (1) to (5) mentioned; for example, an OLED having the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5) or the layers (1), (3), (4) and (5) are likewise suitable.

Those skilled in the art know how suitable materials have to be selected (for example on the basis of electrochemical investigations). Suitable materials for the individual layers and suitable OLED structures are known to those skilled in the art and disclosed, for example, in WO2005/113704.

Furthermore, each of the specified layers of the inventive OLED may be composed of two or more layers. In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the OLED is produced by successive vapor deposition of the individual layers onto a suitable substrate. Suitable substrates are, for example, glass or polymer films. For the vapor deposition, customary techniques may be used, such as thermal evaporation, chemical vapor deposition and others. In an alternative process, the organic layers may be coated from solutions or dispersions in suitable solvents, in which case coating techniques known to those skilled in the art are employed. Compositions which, in addition to the at least one inventive heteroleptic carbene complex, have a polymeric material in one of the layers of the OLED, preferably in the light-emitting layer, are generally applied as a layer by means of solution-mediated processes.

In general, the different layers have the following thicknesses: anode (1) from 500 to 5000 Å, preferably from 1000 to 2000 Å; hole-transporting layer (2) from 50 to 1000 Å, preferably from 200 to 800 Å; light-emitting layer (3) from 10 to 1000 Å, preferably from 100 to 800 Å; electron-transporting layer (4) from 50 to 1000 Å, preferably from 200 to 800 Å; cathode (5) from 200 to 10 000 Å, preferably from 300 to 5000 Å. The position of the recombination zone of holes and electrons in the inventive OLED and thus the emission spectrum of the OLED may be influenced by the relative thickness of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

Use of the inventive heteroleptic carbene complexes in at least one layer of the inventive OLED, preferably as an emitter molecule in the light-emitting layer of the inventive OLEDs, allows OLEDs with high efficiency to be obtained. The efficiency of the inventive OLEDs may additionally be improved by optimizing the other layers. For example, highly efficient cathodes such as Ca, Ba or LiF may be used. Shaped substrates and novel hole-transporting materials which bring about a reduction in the operating voltage or an increase in the quantum efficiency are likewise usable in the inventive OLEDs. Furthermore, additional layers may be present in the OLEDs in order to adjust the energy level of the different layers and to ease electroluminescence.

The inventive OLEDs may be used in all devices in which electroluminescence is useful. Suitable devices are preferably selected from stationary and mobile visual display units. Stationary visual display units are, for example, visual display units of computers, televisions, visual display units in printers, kitchen appliances and advertising panels, illuminations and information panels. Mobile visual display units are, for example, visual display units in cellphones, laptops, digital cameras, vehicles and destination displays on buses and trains.

In addition, the inventive heteroleptic carbene complexes may be used in OLEDs with inverse structure. The inventive heteroleptic carbene complexes are preferably used in these inverse OLEDs again in the light-emitting layer. The structure of inverse OLEDs and the materials customarily used therein are known to those skilled in the art.

The above-described inventive heteroleptic carbene complexes may, in addition to the use in OLEDs, be used as colorants which emit in the visible region of the electromagnetic spectrum on irradiation by light (photoluminescence).

The present application therefore further provides for the use of the above-described inventive heteroleptic carbene complexes for the bulk coloration of polymeric materials.

Suitable polymeric materials are polyvinyl chloride, cellulose acetate, polycarbonates, polyamides, polyurethanes, polyimides, polybenzimidazoles, melamine resins, silicones, polyesters, polyethers, polystyrene, polymethyl methacrylate, polyethylene, polypropylene, polyvinyl acetate, polyacrylonitrile, polybutadiene, polychlorobutadiene, polyisoprene and the copolymers of the monomers listed.

In addition, the above-described inventive heteroleptic carbene complexes may be used in the following applications:

Use of the inventive heteroleptic carbene complexes as or in vat dye(s), for example for coloring natural materials; examples are paper, wood, straw, leather, pelts or natural fiber materials such as cotton, wool, silk, jute, sisal, hemp, flax or animal hairs (for example horsehair) and their conversion products, for example viscose fibers, nitrate silk or copper rayon.

Use of the inventive heteroleptic carbene complexes as colorants, for example for coloring paints, varnishes and other surface coating compositions, paper inks, printing inks, other inks and other colors for drawing and writing purposes.

Use of the inventive heteroleptic carbene complexes as pigmentary dyes, for example for coloring paints, varnishes and other surface coating compositions, paper inks, printing inks, other inks and other colors for drawing and writing purposes.

Use of the inventive heteroleptic carbene complexes as pigments in electrophotography: for example for dry copying systems (Xerox process) and laser printers.

Use of the inventive heteroleptic carbene complexes for security marking purposes, for which high chemical and photochemical stability and, if appropriate, also the luminescence of the substances is of significance. This is preferably for checks, check cards, banknotes, coupons, documents, identification papers and the like, in which a particular, unmistakable color impression is to be achieved.

Use of the inventive heteroleptic carbene complexes as an additive to other colors in which a particular shade is to be achieved; preference is given to particularly brilliant colors.

Use of the inventive heteroleptic carbene complexes for marking articles for machine recognition of these articles using the luminescence, preferably machine recognition of articles for sorting, including, for example, for the recycling of plastics.

Use of the inventive heteroleptic carbene complexes as luminescent dyes for machine-readable markings; preference is given to alphanumeric markings or barcodes.

Use of the inventive heteroleptic carbene complexes for adjusting the frequency of light, for example to convert short-wavelength light into longer-wavelength, visible light.

Use of the inventive heteroleptic carbene complexes in display elements for any kind of display, information and marking purposes, for example in passive display elements, information signs and traffic signs, such as traffic lights.

Use of the inventive heteroleptic carbene complexes in inkjet printers, preferably in homogeneous solution as luminescent ink.

Use of the inventive heteroleptic carbene complexes as a starting material for superconductive organic materials.

Use of the inventive heteroleptic carbene complexes for solid-state luminescent markings.

Use of the inventive heteroleptic carbene complexes for decorative purposes.

Use of the inventive heteroleptic carbene complexes for tracer purposes, for example in biochemistry, medicine, engineering and natural sciences. In this use, the dyes can be bonded covalently to substrates or via secondary valences such as hydrogen bonds or hydrophobic interactions (adsorption).

Use of the inventive heteroleptic carbene complexes as luminescent dyes in high-sensitivity detection methods (cf. C. Aubert, J. Fünfschilling, I. Zschocke-Gränacher and H. Langhals, Z. Analyt. Chem. 320 (1985) 361).

Use of the inventive heteroleptic carbene complexes as luminescent dyes in scintillation devices.

Use of the inventive heteroleptic carbene complexes as dyes or luminescent dyes in optical light-collection systems.

Use of the inventive heteroleptic carbene complexes as dyes or luminescent dyes in luminescent solar collectors (cf. Langhals, Nachr. Chem. Tech. Lab. 28 (1980) 716).

Use of the inventive heteroleptic carbene complexes as dyes or luminescent dyes in luminescence-activated displays (cf. W. Greubel and G. Baur, Elektronik 26 (1977) 6).

Use of the inventive heteroleptic carbene complexes as dyes or luminescent dyes in cold light sources for light-induced polymerization for the production of plastics.

Use of the inventive heteroleptic carbene complexes as dyes or luminescent dyes for materials testing, for example in the production of semiconductor circuits.

Use of the inventive heteroleptic carbene complexes as dyes or luminescent dyes for the investigation of microstructures of integrated semiconductor components.

Use of the inventive heteroleptic carbene complexes as dyes or luminescent dyes in photoconductors.

Use of the inventive heteroleptic carbene complexes as dyes or luminescent dyes in photographic processes.

Use of the inventive heteroleptic carbene complexes as dyes or luminescent dyes in display, illumination or image conversion systems, in which excitation occurs by means of electrons, ions or UV radiation, for example in luminescent displays, Braun tubes or in fluorescent tubes.

Use of the inventive heteroleptic carbene complexes as dyes or luminescent dyes as part of an integrated semiconductor circuit, the dyes being used as such or in conjunction with other semiconductors, for example in the form of epitaxy.

Use of the inventive heteroleptic carbene complexes as dyes or luminescent dyes in chemiluminescent systems, for example in chemiluminescent illumination rods, in luminescent immunoassays or other luminescent detection methods.

Use of the inventive heteroleptic carbene complexes as dyes or luminescent dyes as signal colors, preferably for the optical emphasis of inscriptions and drawings or other graphical products, for individualizing signs and other articles in which a particular optical color impression is to be achieved.

Use of the inventive heteroleptic carbene complexes as dyes or luminescent dyes in dye lasers, preferably as luminescent dyes for generating laser beams.

Use of the inventive heteroleptic carbene complexes as active substances for nonlinear optics, for example for frequency doubling and frequency tripling of laser light.

Use of the inventive heteroleptic carbene complexes as rheology improvers.

Use of the inventive heteroleptic carbene complexes as dyes in photovoltaic applications for the conversion of electromagnetic radiation to electrical energy.

The invention claimed is:

1. A heteroleptic carbene complex of the general formula (I)

$$M^1[\text{carbene}]_n[\text{het}]_m \qquad (I)$$

comprising both carbene ligands and heterocyclic noncarbene ligands,
in which the symbols are each defined as follows:
$M^1$ is a metal atom selected from the group consisting of Ir(III), Os(II), or Rh(III);
n is the number of carbene ligands, where n is 2, where the carbene ligands may be the same or different;
m is the number of heterocyclic noncarbene ligands, where is 1;
where
carbene is a carbene ligand of the general formula (II)

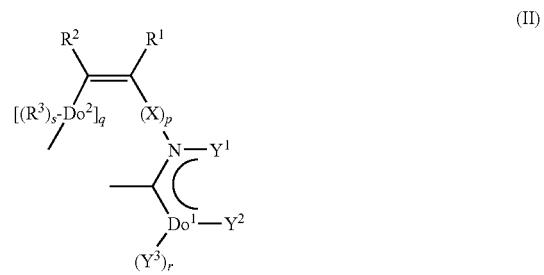

where the symbols in the carbine ligand of the general formula II are each defined as follows:
$Do^1$ is N
r is 1;
p is 0;
q is 0;
$Y^1$ and $Y^2$ together form a bridge between the donor atom $Do^1$ and the nitrogen atom N, said bridge having two carbon atoms,
$R^1$ and $R^2$ together form a bridge having a total of from four carbon atoms, so that the group

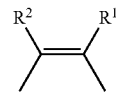

forms a six-membered ring which, in addition to the double bond already present has two further double bonds, and may optionally be substituted by alkyl or aryl groups and/or groups with donor or acceptor action;

$Y^3$ is hydrogen, an alkyl, alkynyl or alkenyl radical, or

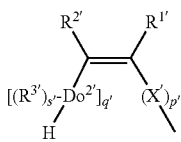

where $Do^2$, $q'$, $s'$ $R^{3'}$, $R^{1'}$, $R^{2'}$, $X'$ and $p'$ are each independently as defined for $Do^2$, $q$, $s$, $R^3$, $R^1$, $R^2$, $X$ and $p$,
and
het is a heterocyclic noncarbene ligand of the general formula (III)

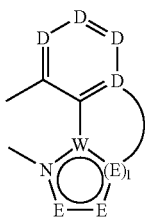

(III)

in which the symbols in the ligand het of the general formula III are each defined as follows:
D are each independently $CR^{34}$ or N;
W is C, N, or P;
E are each independently $CR^{35}$, N, $NR^{36}$, S, O, P or $PR^{37}$;
l is 1 or 2;
$R^{34}$, $R^{35}$, $R^{37}$ are each independently H, an alkyl, aryl, heteroaryl, alkynyl or alkenyl radical, $R^{36}$ is H, an alkyl, heteroaryl, alkynyl, or alkenyl radical or an aryl radical with a base structure selected from phenyl, naphthyl, anthracenyl and phenanthrenyl which base structure is unsubstituted, or in each case 2 $R^{34}$, $R^{35}$, $R^{36}$ or $R^{37}$ radicals together form a fused ring which may optionally comprise at least one heteroatom, or $R^{34}$, $R^{35}$, $R^{36}$ or $R^{37}$ is a radical having donor or acceptor action;
where the dotted line means an optional bridge between one of the D groups and one of the E groups; where the bridge may be defined as follows:
alkylene, arylene, heteroarylene, alkynylene, alkenylene, $NR^{38}$, $PR^{39}$, $BR^{40}$, O, S, SO, $SO_2$, $SiR^{41}R^{42}$, CO, CO—O, O—CO and $(CR^{43}R^{44})_v$, where one or more nonadjacent ($CR^{43}$ $R^{44}$) groups may be replaced by $NR^{38}$, $PR^{39}$, $BR^{40}$, O, S, SO, $SO_2$, $SiR^{41}R^{42}$, CO, CO—O, or O—CO, where
v is from 2 to 10;
and
$R^{38}$, $R^{39}$, $R^{40}$, $R^{41}$, $R^{42}$ $R43$ $R^{44}$ are each H, alkyl, aryl, heteroaryl, alkenyl, or alkynyl.

2. The carbene complex according to claim 1, wherein the moiety

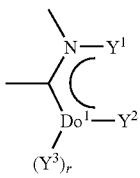

is selected from the group consisting of

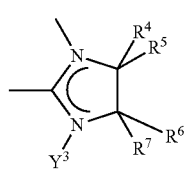

a

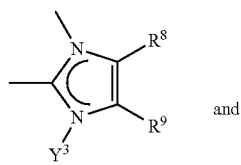

and b

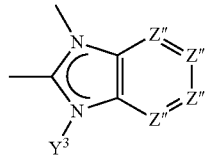

c in which the symbols are each defined as follows:
$Z''$ are each independently $CR^{10}$ or N;
$R^4$, $R^5$, $R^6$, $R^7$, $R^8$, and R9 are each hydrogen, alkyl, aryl, heteroaryl, alkynyl or alkenyl or a substituent with donor or acceptor action;
$R^{10}$ is hydrogen, alkyl, aryl, heteroaryl, alkynyl or alkenyl, or in each case 2 $R^{10}$ radicals together form a fused ring which may optionally comprise at least one heteroatom, or $R^{10}$ is a radical with donor or acceptor action;
in addition, $R^4$ or $R^5$ in the moiety a, $R^8$ in the moiety b, one of the $R^{10}$ radicals in the moiety c and $R^{11}$ in the moiety d may be bonded to $R^1$ via a bridge, where the bridge may be defined as follows:
alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent ($CR^{21}$ $R^{22}$) groups may be replaced by $NR^{18}$, $PR^{19}$, $BR^{20}$, O, S, SO, $SO_2$, $SiR^{30}R^{31}$, CO, CO—O, or O—CO, where
x is from 2 to 10; and
$R^{18}$, $R^{19}$, $R_{20}$, $R^{21}$, $R^{22}$, $R^{30}$ $R^{31}$ are each H, alkyl, aryl, heteroaryl, alkenyl, or alkynyl.

3. The carbene complex according to claim 1, wherein the moiety

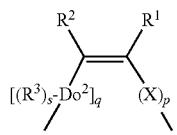

has the structure

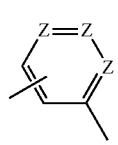

in which the symbols are each defined as follows:

Z are each independently $CR^{12}$;

$R^{12}$ in the Z groups are each independently H, an alkyl, aryl, heteroaryl, alkynyl, or alkenyl radical, or in each case 2 $R^{12}$ radicals together form a fused ring which may optionally comprise at least one heteroatom, or $R^{12}$ is a radical with donor or acceptor action.

4. The carbene complex according to claim 1, wherein the at least one carbene ligand is selected from the group consisting of

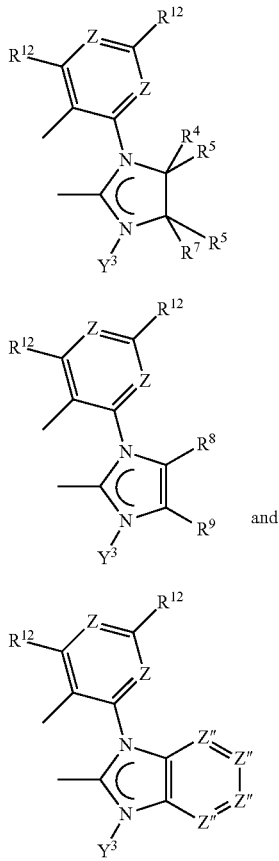

aa ab ac and where the symbols are each defined as follows:
$Y^3$ is an alkyl, alkynyl or alkenyl radical
or
a group of the following structure

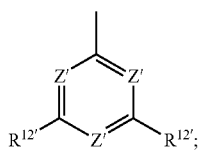

Z is the same or different and is $CR^{12}$;
Z' is the same or different and is $CR^{12'}$ or N;
Z" is the same or different and is $CR^{10}$ or N;
$R^{12}$, $R^{12'}$ are the same or different and are each independently H, an alkyl, aryl, heteroaryl, alkynyl or alkenyl radical, or in each case 2 $R^{12}$ or $R^{12'}$ radicals together form a fused ring which may optionally comprise at least one heteroatom, or $R^{12}$ or $R^{12'}$ is a radical with donor or acceptor action;

$R_4$, $R^5$, $R^6$, $R^7$, $R^8$ and $R^9$ are each hydrogen alkyl, aryl, heteroaryl, alkynyl or alkenyl, or a radical with donor or acceptor action;

$R^{10}$ in the Z" groups are each independently H, alkyl, aryl, heteroaryl, alkynyl or alkenyl, or in each case 2 $R^{10}$ radicals together form a fused ring which may optionally comprise at least one heteroatom, or $R^{10}$ is a radical with donor or acceptor action.

5. The carbene complex according to claim 1, wherein the heterocyclic noncarbene ligand het is selected from the group consisting of

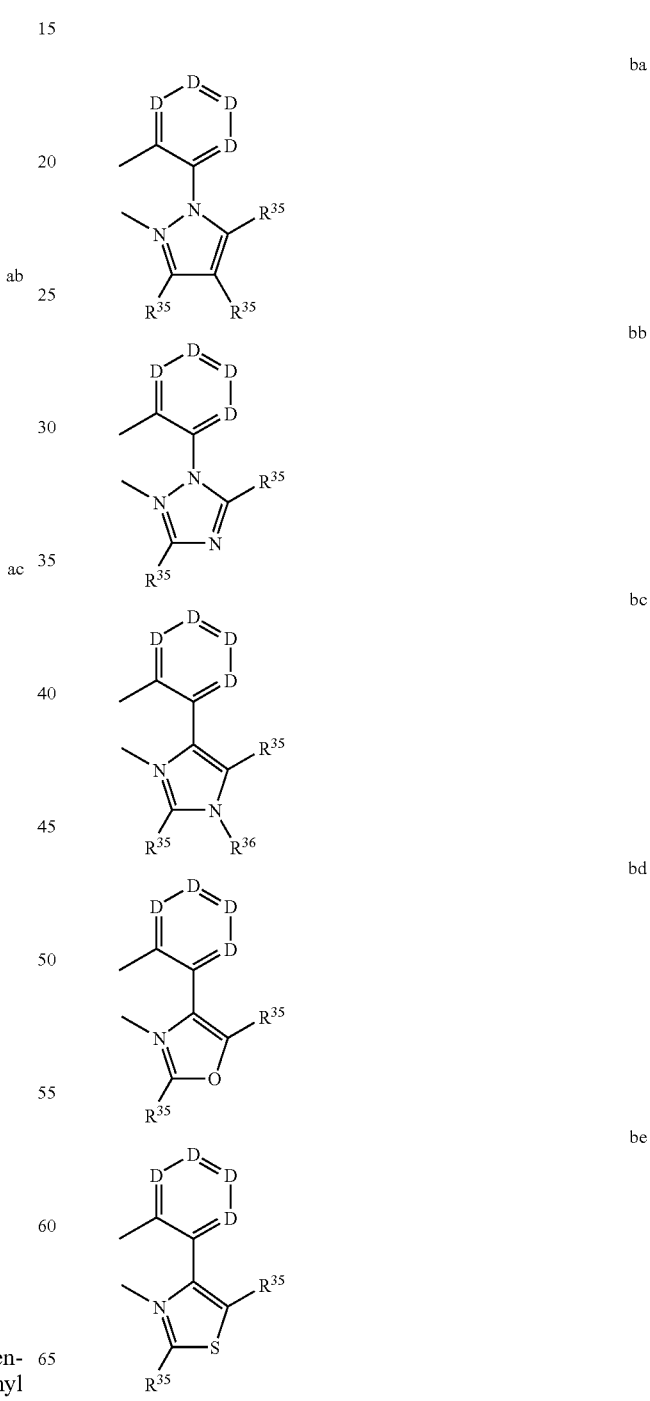

ba bb bc bd be bf 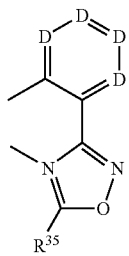
bg 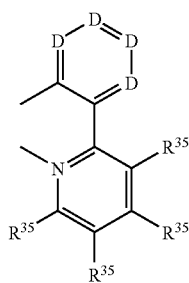
bh 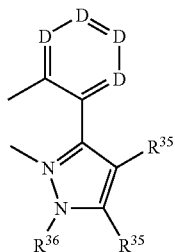
bi 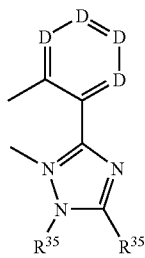
bj 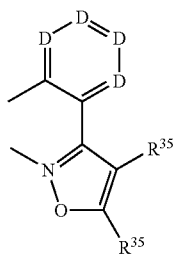
bk 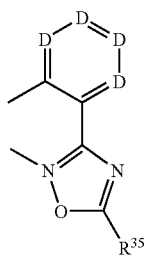
bl 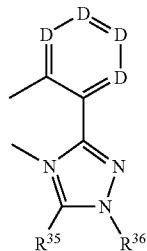
bm 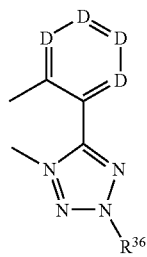
bn 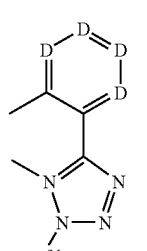
bo 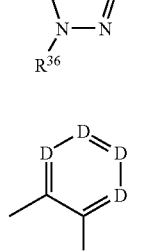
bp 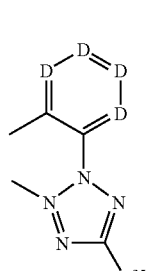
bq 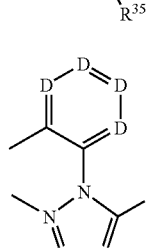

br

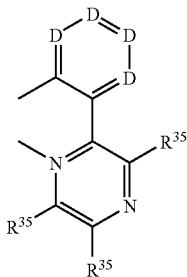

bs

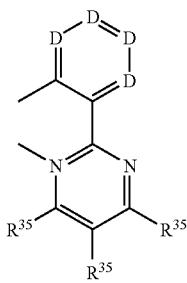

bt

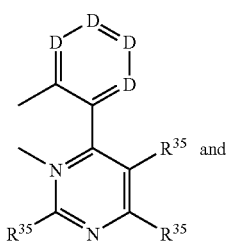 and bu

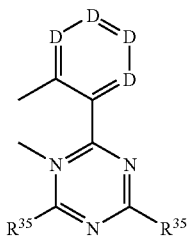

where
D are each independently CR$^{34}$ or N;
R$^{34}$ and R$^{35}$, are each independently H, an alkyl, aryl, heteroaryl, alkynyl or alkenyl radical, R$^{36}$ is H, an alkyl, heteroaryl, alkynyl, or alkenyl radical or an aryl radical with a base structure selected from phenyl, naphthyl, anthracenyl and phenanthrenyl which base structure is unsubstituted, or in each case 2 R$^{34}$, R$^{35}$ or R$^{36}$ radicals together form a fused ring which may optionally comprise at least one heteroatom, or R$^{34}$, R$^{35}$ or R$^{36}$ is a radical with donor or acceptor action.

6. The carbene complex according to claim 1, wherein M1 is Ir(III) and n =2 and m =1.

7. The carbene complex according to claim 6, wherein the carbene complex has the general formula (Ii):

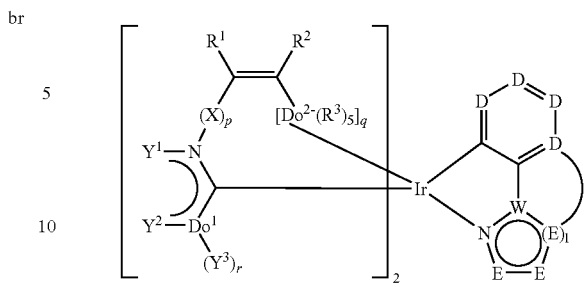

where the symbols in the carbene complexes of the general formula (Ii) are each defined as follows:
Do$^1$ is N;
r is 1;
p is 0;
q is 0;
Y$^1$ and Y$^2$ together form a bridge between the donor atom Do$^1$ and the nitrogen atom N which has two carbon atoms,
R$^1$ and R$^2$ together form a bridge having a total of from four carbon atoms, so that the group

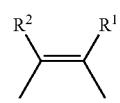

forms a six-membered ring which in addition to the double bond already present has two further double bonds, and may optionally be substituted by alkyl or aryl groups and/or groups with donor or acceptor action;
Y$^3$ is hydrogen, an alkyl, alkynyl or alkenyl radical,
or

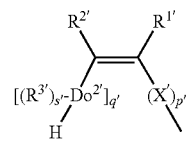

where Do$^{2'}$, q', s', R$^{3'}$, R$^{1'}$, R$^{2'}$, X' and p' are each independently as defined for Do$^2$, q, s, R$^3$, R', R$^2$, X and p;
D are each independently CR$^{34}$ or N;
W is C, N, or P;
E are each independently CR$^{35}$, N, NR$^{36}$, S, O, P or PR$^{37}$;
l is 1 or 2;
R$^{34}$, R$^{35}$, R$^{37}$ are each independently H, an alkyl, aryl, heteroaryl, alkynyl or alkenyl radical, R$^{36}$ is H, an alkyl, heteroaryl, alkynyl, or alkenyl radical or an aryl radical with a base structure selected from phenyl, naphthyl, anthracenyl and phenanthrenyl which base structure is unsubstituted, or in each case 2 R$^{34}$, R$^{35}$, R$^{36}$ or R$^{37}$ radicals together form a fused ring which may optionally comprise at least one heteroatom, or R$^{34}$, R$^{35}$, R$^{36}$ or R$^{37}$ is a radical with donor or acceptor action;
where the radicals, groups and indices R$^1$, R$^2$, R$^3$, Do$^1$, Do$^2$, Y$^1$, Y$^2$, Y$^3$, X, p. q and r in the carbene ligands in the compounds of the general formula Ii may each be the same or different;
where the dotted line means an optional bridge between one of the D groups and one of the E groups; where the bridge may be defined as follows:

alkylene, arylene, heteroarylene, alkynylene, alkenylene, $NR^{38}$, $PR^{39}$, $BR^{40}$, O, S, SO, $SO_2$, $SiR^{41}R^{42}$, CO, CO—O, O—CO and $(CR^{43}R^{44})$ where one or more non-adjacent $(CR^{43}R^{44})$ groups may be replaced by $NR^{38}$, $PR^{39}$, $BR^{40}$, O, S, SO, $SO_2$, $SiR^{41}R^{42}$, CO, CO—O, or O—CO, where v is from 2 to 10;
and
$R^{38}$, $R^{39}$, $R^{40}$, $R^{41}$, $R^{42}$, $R^{43}$, $R^{44}$ are H, alkyl, aryl, heteroaryl, alkenyl, or alkynyl.

8. A process for preparing heteroleptic carbene complexes of the general formula I according to claim 1, wherein the preparation comprises the following step:

reaction of at least one ligand precursor of the general formula (IV)

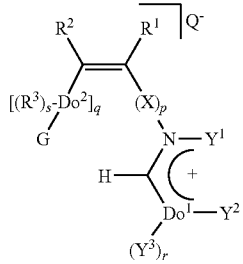

(III)

in which
$Q^-$ is a monoanionic counterion, preferably halide;
and
G is H;
and
the further symbols in the ligand precursor of the general formula IV are each defined as follows:
$Do^1$ is N;
r is 1;
p is 0;
q is 0;
$Y^1$ and $Y^2$ together form a bridge between the donor atom $Do^1$ and the nitrogen atom N, said bridge having two carbon atoms
$R^1$ and $R^2$ together form a bridge having a total of from four carbon atoms, so that the group

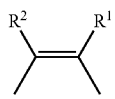

forms a six-membered ring which, in addition to the double bond already present has two further double bonds, and may optionally be substituted by alkyl or aryl groups and/or groups with donor or acceptor action;

$Y^3$ is hydrogen, an alkyl, alkynyl or alkenyl radical, or

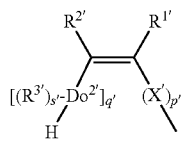

where $Do^{2'}$, q', s', $R^{3'}$, $R^{1'}$, $R^{2'}$, X' and p' are each independently as defined for $Do^2$, q, s, $R^3$, $R^1$, $R^2$, X and p;
and
at least one ligand precursor of the general formula V

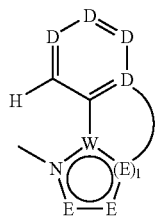

in which:
D are each independently $CR^{34}$ or N;
W is C, N, or P;
E are each independently $CR^{35}$, N, $NR^{36}$, S, O, P or $PR^{37}$;
l is 1 or 2;
$R^{34}$, $R^{35}$, $R^{37}$ are each independently H, an alkyl, aryl, heteroaryl, alkynyl or alkenyl radical, $R^{36}$ is H, an alkyl, heteroaryl, alkynyl, or alkenyl radical or an aryl radical with a base structure selected from phenyl, naphthyl, anthracenyl and phenanthrenyl which base structure is unsubstituted, or in each case 2 $R^{34}$, $R^{35}$, $R^{36}$ or $R^{37}$ radicals together form a fused ring which may optionally comprise at least one heteroatom, or $R^{34}$, $R^{35}$, $R^{36}$ or $R^{37}$ is a radical with donor or acceptor action;
with a metal complex comprising at least one metal $M^{1'}$, where $M^{1'}$ is defined as follows:
$M^{1'}$ is a metal atom selected from the group consisting of Ir(III), Os(II), and Rh(III).

9. The process according to claim 8, wherein the metal $M^1$ used is Ir(III)

10. An organic light-emitting diode comprising at least one heteroleptic carbene complex according to claim 1.

11. A light-emitting layer comprising at least one heteroleptic carbene complex according to claim 1.

12. An organic light-emitting diode comprising at least one light-emitting layer according to claim 11.

13. A device selected from the group consisting of stationary visual display units mobile visual display units, comprising at least one organic light-emitting diode according to claim 10.

14. A device selected from the group consisting of stationary visual display units and mobile visual display units comprising at least one organic light-emitting diode according to claim 12.

* * * * *